(12) United States Patent
Skerven

(10) Patent No.: US 8,221,505 B2
(45) Date of Patent: Jul. 17, 2012

(54) PROSTHESIS HAVING A SLEEVE VALVE

(75) Inventor: Gregory J. Skerven, Kernersville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 413 days.

(21) Appl. No.: 11/709,518

(22) Filed: Feb. 22, 2007

(65) Prior Publication Data

US 2008/0208314 A1  Aug. 28, 2008

(51) Int. Cl.
  *A61F 2/04*  (2006.01)
  *A61F 2/82*  (2006.01)
(52) U.S. Cl. ............... 623/23.68; 623/23.64; 623/23.65; 623/23.66; 623/23.7
(58) Field of Classification Search ............... 623/1.24, 623/23.68, 1.26, 23.64, 23.65, 23.66, 23.7, 623/1.13, 1.49
See application file for complete search history.

(56) References Cited

U.S. PATENT DOCUMENTS

| | | |
|---|---|---|
| 3,868,956 A | 3/1975 | Alfidi et al. |
| 3,890,977 A | 6/1975 | Wilson |
| 3,996,938 A | 12/1976 | Clark, III |
| 4,149,911 A | 4/1979 | Clabburn |
| 4,271,827 A | 6/1981 | Angelchik |
| 4,306,318 A | 12/1981 | Mano et al. |
| 4,425,908 A | 1/1984 | Simon |
| 4,445,896 A | 5/1984 | Gianturco |
| 4,494,531 A | 1/1985 | Gianturco |
| 4,503,569 A | 3/1985 | Dotter |
| 4,512,338 A | 4/1985 | Balko et al. |
| 4,553,545 A | 11/1985 | Maass et al. |
| 4,560,374 A | 12/1985 | Hammerslag |
| 4,572,186 A | 2/1986 | Gould et al. |
| 4,580,568 A | 4/1986 | Gianturco |
| 4,636,313 A | 1/1987 | Vaillancourt |
| 4,649,922 A | 3/1987 | Wiktor |
| 4,655,771 A | 4/1987 | Wallsten |
| 4,657,530 A | 4/1987 | Buchwald et al. |
| 4,665,918 A | 5/1987 | Garza et al. |
| 4,681,110 A | 7/1987 | Wiktor |
| 4,687,468 A | 8/1987 | Gianturco |

(Continued)

FOREIGN PATENT DOCUMENTS

CZ    5985 U1   4/1997

(Continued)

OTHER PUBLICATIONS

Gray, Henry, Grays Anatomy, 874 (Barnes & Noble Books, 15 ed.).

(Continued)

*Primary Examiner* — Howie Matthews
*Assistant Examiner* — Suba Ganesan
(74) *Attorney, Agent, or Firm* — Brinks Hofer Gilson & Lione

(57) ABSTRACT

Disclosed is a pressure sensitive prosthesis that includes a tubular member having a passageway extending therethrough and a sleeve attached about one end of the tubular member. The sleeve functions as a one-way valve to permit fluid flowing through the sleeve lumen in a first, distal direction and under a first pressure, while collapsing in response to fluid flowing in a second direction when the pressure thereof exceeds that of the first direction or pressure. One aspect of the invention includes a first opening and a second opening configured for allowing fluid flow from the passage to the lumen in the first direction.

15 Claims, 14 Drawing Sheets

U.S. PATENT DOCUMENTS

| | | | |
|---|---|---|---|
| 4,699,611 A | 10/1987 | Bowden | |
| 4,716,900 A | 1/1988 | Ravo et al. | |
| 4,719,916 A | 1/1988 | Ravo | |
| 4,723,549 A | 2/1988 | Wholey et al. | |
| 4,729,766 A | 3/1988 | Bergentz et al. | |
| 4,732,152 A | 3/1988 | Wallsten et al. | |
| 4,733,665 A | 3/1988 | Palmaz | |
| 4,739,762 A | 4/1988 | Palmaz | |
| 4,762,128 A | 8/1988 | Rosenbluth | |
| 4,768,507 A | 9/1988 | Fichell et al. | |
| 4,776,337 A | 10/1988 | Palmaz | |
| 4,793,348 A | 12/1988 | Palmaz | |
| 4,794,928 A | 1/1989 | Kletschka | |
| 4,800,882 A | 1/1989 | Gianturco | |
| 4,820,298 A | 4/1989 | Leveen et al. | |
| 4,825,861 A | 5/1989 | Koss | |
| 4,830,003 A | 5/1989 | Wolff et al. | |
| 4,846,836 A | 7/1989 | Reich | |
| 4,848,343 A | 7/1989 | Wallsten et al. | |
| 4,850,999 A | 7/1989 | Pianck | |
| 4,856,516 A | 8/1989 | Hillstead | |
| 4,857,069 A | 8/1989 | Kira | |
| 4,877,030 A | 10/1989 | Beck et al. | |
| 4,878,906 A | 11/1989 | Lindemann et al. | |
| 4,886,062 A | 12/1989 | Wiktor | |
| 4,907,336 A | 3/1990 | Gianturco | |
| 4,913,141 A | 4/1990 | Hillstead | |
| 4,921,484 A | 5/1990 | Hillstead | |
| 4,922,905 A | 5/1990 | Strecker | |
| 4,955,899 A | 9/1990 | Della Corna et al. | |
| 4,957,508 A | 9/1990 | Kaneko et al. | |
| 4,969,458 A | 11/1990 | Wiktor | |
| 4,973,301 A | 11/1990 | Nissenkorn | |
| 5,015,253 A | 5/1991 | MacGregor | |
| 5,019,090 A | 5/1991 | Pinchuk | |
| 5,019,102 A | 5/1991 | Hoene | |
| 5,026,377 A | 6/1991 | Burton et al. | |
| 5,035,706 A | 7/1991 | Giantureo et al. | |
| 5,041,126 A | 8/1991 | Gianturco | |
| 5,052,998 A | 10/1991 | Zimmon | |
| 5,057,092 A | 10/1991 | Webster, Jr. | |
| 5,064,435 A | 11/1991 | Porter | |
| 5,067,957 A | 11/1991 | Jervis | |
| 5,071,407 A | 12/1991 | Termin et al. | |
| 5,078,736 A | 1/1992 | Behl | |
| 5,089,006 A | 2/1992 | Stiles | |
| 5,108,416 A | 4/1992 | Ryan et al. | |
| 5,112,900 A | 5/1992 | Buddenhagen et al. | |
| 5,123,917 A | 6/1992 | Lee | |
| 5,129,910 A | 7/1992 | Phan et al. | |
| 5,133,732 A | 7/1992 | Wiktor | |
| 5,135,536 A | 8/1992 | Hillstead | |
| 5,158,548 A | 10/1992 | Lau et al. | |
| 5,176,626 A | 1/1993 | Soehendra | |
| 5,221,261 A | 6/1993 | Termin et al. | |
| 5,258,000 A | 11/1993 | Gianturco | |
| 5,282,823 A | 2/1994 | Schwartz et al. | |
| 5,282,824 A | 2/1994 | Gianturco | |
| 5,306,300 A | 4/1994 | Berry | |
| 5,314,444 A | 5/1994 | Gianturco | |
| 5,314,473 A * | 5/1994 | Godin | 623/23.68 |
| 5,316,023 A | 5/1994 | Palmaz et al. | |
| 5,316,543 A | 5/1994 | Eberbach | |
| 5,330,500 A | 7/1994 | Song | |
| 5,334,208 A | 8/1994 | Soehendra et al. | |
| 5,334,210 A | 8/1994 | Gianturco | |
| 5,360,443 A | 11/1994 | Barone et al. | |
| 5,378,239 A | 1/1995 | Termin et al. | |
| 5,405,316 A | 4/1995 | Magram | |
| 5,405,377 A | 4/1995 | Cragg | |
| 5,411,552 A | 5/1995 | Andersen et al. | |
| 5,413,601 A | 5/1995 | Keshelava | |
| 5,443,499 A | 8/1995 | Schmitt | |
| 5,496,277 A | 3/1996 | Termin et al. | |
| 5,500,014 A | 3/1996 | Quijano et al. | |
| 5,507,771 A | 4/1996 | Gianturco | |
| 5,534,287 A | 7/1996 | Lukic | |
| 5,545,211 A | 8/1996 | An et al. | |
| 5,645,559 A | 7/1997 | Hichtman et al. | |
| 5,647,843 A | 7/1997 | Mesrobian et al. | |
| 5,653,727 A | 8/1997 | Wiktor | |
| 5,662,713 A | 9/1997 | Andersen et al. | |
| 5,665,115 A | 9/1997 | Cragg | |
| 5,667,523 A | 9/1997 | Bynon et al. | |
| 5,674,241 A | 10/1997 | Bley et al. | |
| 5,683,448 A | 11/1997 | Cragg | |
| 5,716,393 A | 2/1998 | Lindenberg et al. | |
| 5,733,325 A | 3/1998 | Robinson et al. | |
| 5,733,330 A | 3/1998 | Cox | |
| 5,741,333 A | 4/1998 | Frid | |
| 5,746,766 A | 5/1998 | Edoga | |
| 5,755,769 A | 5/1998 | Richard et al. | |
| RE35,849 E | 7/1998 | Soehendra | |
| 5,782,904 A | 7/1998 | White et al. | |
| 5,788,626 A | 8/1998 | Thompson | |
| 5,817,102 A | 10/1998 | Johnson et al. | |
| 5,824,042 A | 10/1998 | Lombardi et al. | |
| 5,824,049 A | 10/1998 | Ragheb | |
| 5,843,158 A | 12/1998 | Lenker et al. | |
| 5,843,170 A | 12/1998 | Ahn | |
| 5,861,036 A | 1/1999 | Godin | |
| 5,876,445 A | 3/1999 | Andersen et al. | |
| 5,876,448 A | 3/1999 | Thompson et al. | |
| 5,876,450 A | 3/1999 | Johlin, Jr. | |
| 5,879,382 A | 3/1999 | Boneau | |
| 5,922,019 A | 7/1999 | Hankh et al. | |
| 5,968,070 A | 10/1999 | Bley et al. | |
| 5,993,482 A | 11/1999 | Chuter | |
| 6,010,529 A | 1/2000 | Herweck et al. | |
| 6,027,525 A | 2/2000 | Suh et al. | |
| 6,036,725 A | 3/2000 | Avellanet | |
| 6,132,471 A * | 10/2000 | Johlin, Jr. | 623/23.64 |
| 6,162,244 A | 12/2000 | Braun et al. | |
| 6,254,642 B1 | 7/2001 | Taylor | |
| 6,264,700 B1 | 7/2001 | Kilcoyne et al. | |
| 6,302,917 B1 * | 10/2001 | Dua et al. | 623/23.68 |
| 6,494,909 B2 | 12/2002 | Greenhalgh | |
| 6,746,489 B2 * | 6/2004 | Dua et al. | 623/23.68 |
| 6,764,518 B2 | 7/2004 | Godin | |
| 7,118,600 B2 * | 10/2006 | Dua et al. | 623/23.68 |
| 7,220,237 B2 * | 5/2007 | Gannoe et al. | 604/8 |
| 7,347,875 B2 * | 3/2008 | Levine et al. | 623/23.65 |
| 2001/0020190 A1 | 9/2001 | Taylor | |
| 2003/0060894 A1 * | 3/2003 | Dua et al. | 623/23.68 |
| 2003/0212450 A1 | 11/2003 | Schlick | |
| 2004/0093070 A1 * | 5/2004 | Hojeibane et al. | 623/1.15 |
| 2004/0102855 A1 | 5/2004 | Shank | |
| 2004/0199262 A1 * | 10/2004 | Dua et al. | 623/23.7 |
| 2005/0096734 A1 * | 5/2005 | Majercak et al. | 623/1.24 |
| 2005/0096735 A1 * | 5/2005 | Hojeibane et al. | 623/1.24 |
| 2005/0267560 A1 * | 12/2005 | Bates | 623/1.1 |
| 2007/0016306 A1 * | 1/2007 | Dua et al. | 623/23.68 |

FOREIGN PATENT DOCUMENTS

| | | |
|---|---|---|
| DE | 8905127 U1 | 8/1989 |
| EP | 0 480667 B1 | 4/1992 |
| EP | 0 808614 B1 | 11/1997 |
| EP | 0275535 A1 | 7/1998 |
| EP | 0 857471 A2 | 8/1998 |
| EP | 1 704 834 A1 | 9/2006 |
| FR | 1 576 374 | 8/1969 |
| FR | 2 513 111 | 3/1983 |
| GB | 2069339 A | 8/1981 |
| JP | 3-198844 A | 8/1991 |
| JP | 7-275369 A | 10/1995 |
| JP | 10-211287 | 8/1998 |
| JP | 10211287 A | 8/1998 |
| RU | 1600785 A1 | 10/1990 |
| SU | 1292761 A1 | 2/1987 |
| WO | WO 91/01117 A1 | 2/1991 |
| WO | WO 96/07370 | 3/1996 |
| WO | WO 96/29954 | 10/1996 |
| WO | WO 96/29954 A1 | 10/1996 |
| WO | WO 00/32137 A1 | 6/2000 |
| WO | WO 2005/032422 A1 | 4/2005 |
| WO | WO 2007/142833 A1 | 12/2007 |

OTHER PUBLICATIONS

Palliation of Gastroesphogeal Carcinoma With Endoscopic Insertion of a New Antireflux Prosthesis, Jose Valbuena M.D. Gastrointestinal Endoscopy, vol. 30, No. 4, 1984.

Esophageal Stent with Antireflux Valve for Tumors Involving the Cardia; Work in Progress; M. Kocher, M. Dloughy, C. Neoral, E. Buriankova, A. Gryga, M. Duda, & R. Aujesky, JVIR; Nov.-Dec., 1998; pp. 1007-1010.

Trial Use of a Gore-Tex Covered Ultralrex Stent with Reflux Preventive Action for Cardioesophegeal Cancer, Y. Mizumato, K. Matsuda, Y. Itoh, M. Kuno, M. Mizumoto, N. Shima, M. Naoki, H. Satake, T. Maekawa, Y. Kajitani & Y. Kogawa.

Cook-Z® Stents; Gianturco-Rosch Covered Esophageal Design; Cook Diagnostic and Interventional Products.

International Search Report dated May 18, 2006 from International Application No. PCT/US2006/003200.

International Search Report mailed May 30, 2008 for International Application No. PCT/US2008/053633.

Mizumoto, Y. et al.; "Application of GORE-TEX Covered Ultraflex Stent With Back Flow Prevention to Lower Esophageal Cancer;" Gastroenterological Endoscopy 38 (Suppl. 2): 1819, Aug. 1996, Abstract VW 3 (English translation of Abstract).

Valbuena, J.; "Endoscopic Palliative Treatment of Esophageal and Cardial Cancer: A New Antireflux Prosthesis;" Cancer 53(4):993-998; Feb. 15, 1984.

Valbuena, J.; "Endoscopic Palliative Treatment of Esophageal and Cardial Cancer: A Study of 40 Cases: A New Antireflux Prosthesis is Presented;" Proceedings of the 13th International Cancer Congress, Seattle, WA, Sep. 8-15, 1982; p. 695; Abstract 3980.

Valbuena, J.; "Malignant Esophagopulmonary Fistula Treated by Fiberoptic Intubation of a Prosthesis;" Gastrointestinal Endoscopy 31(4):281-283; 1985.

Valbuena, J.V. et al.; "Prótesis Peroral Endoscópica en el Tratamiento de Cáncer de Esófago y Cardias;" Rev. Col. Gastroent. 2(1):17-22; Mar. 1987; with English translation entitled "Endoscopic Peroral Prosthesis in the Treatment of Esophageal and Cardial Cancer."

* cited by examiner

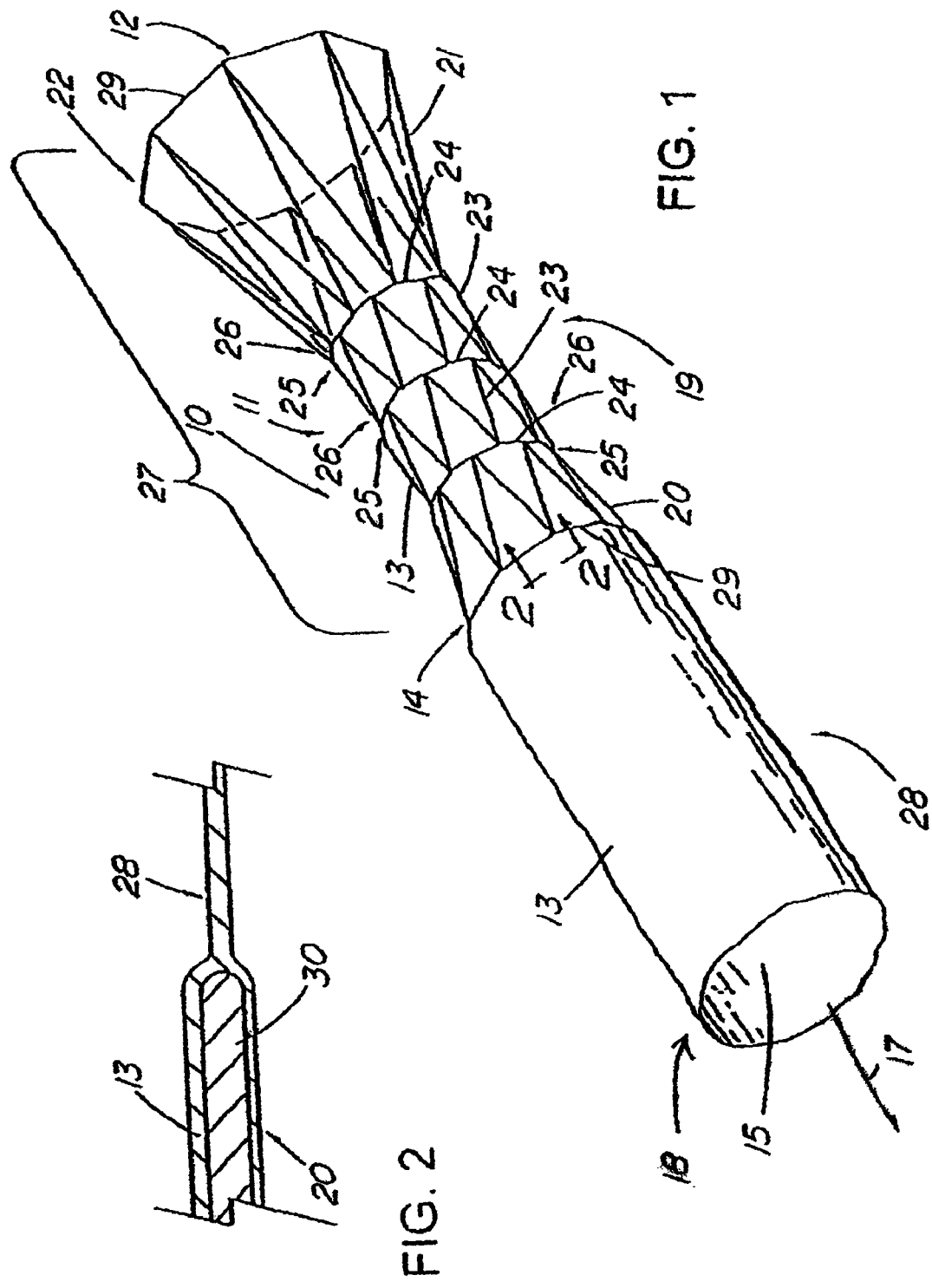

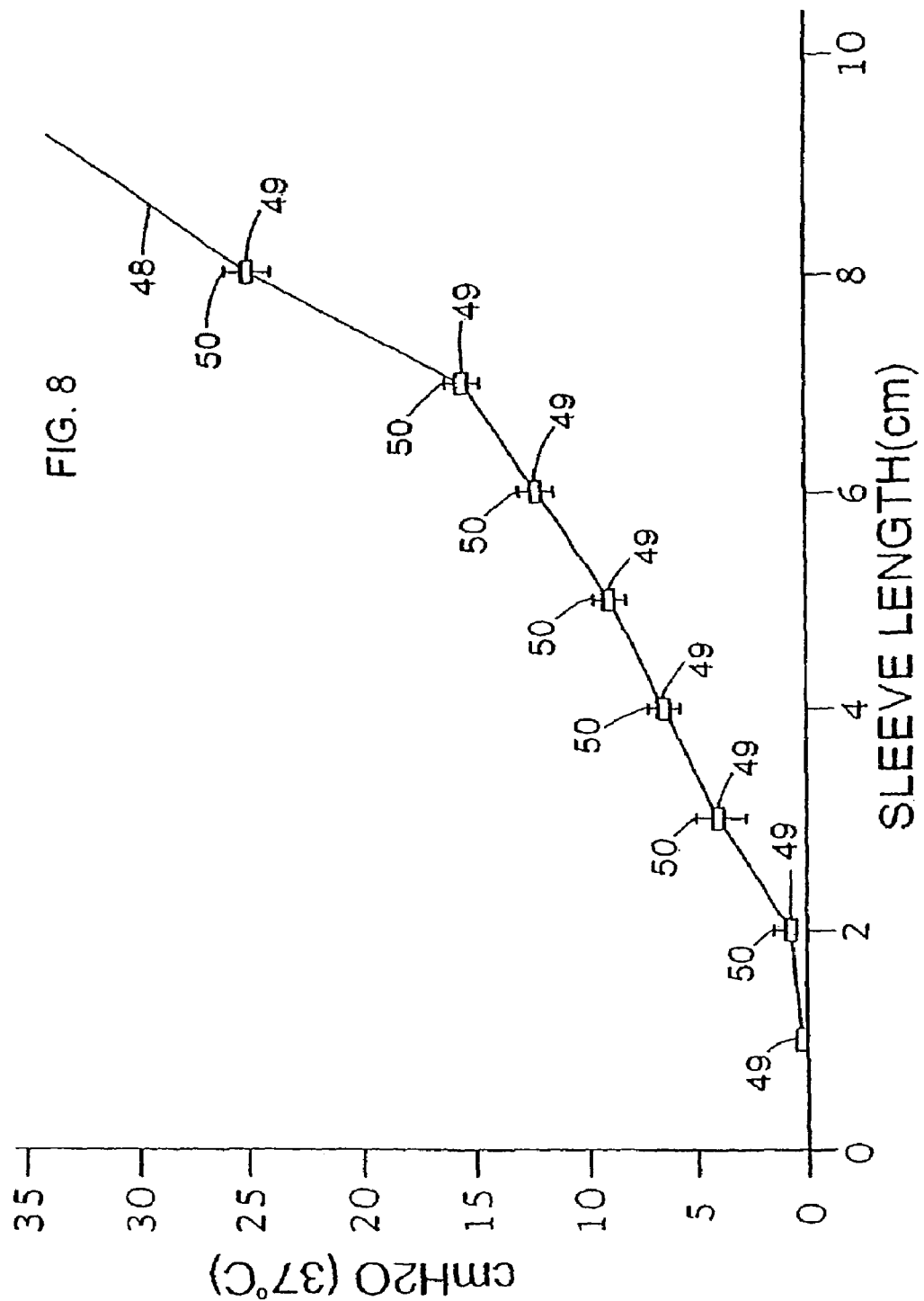

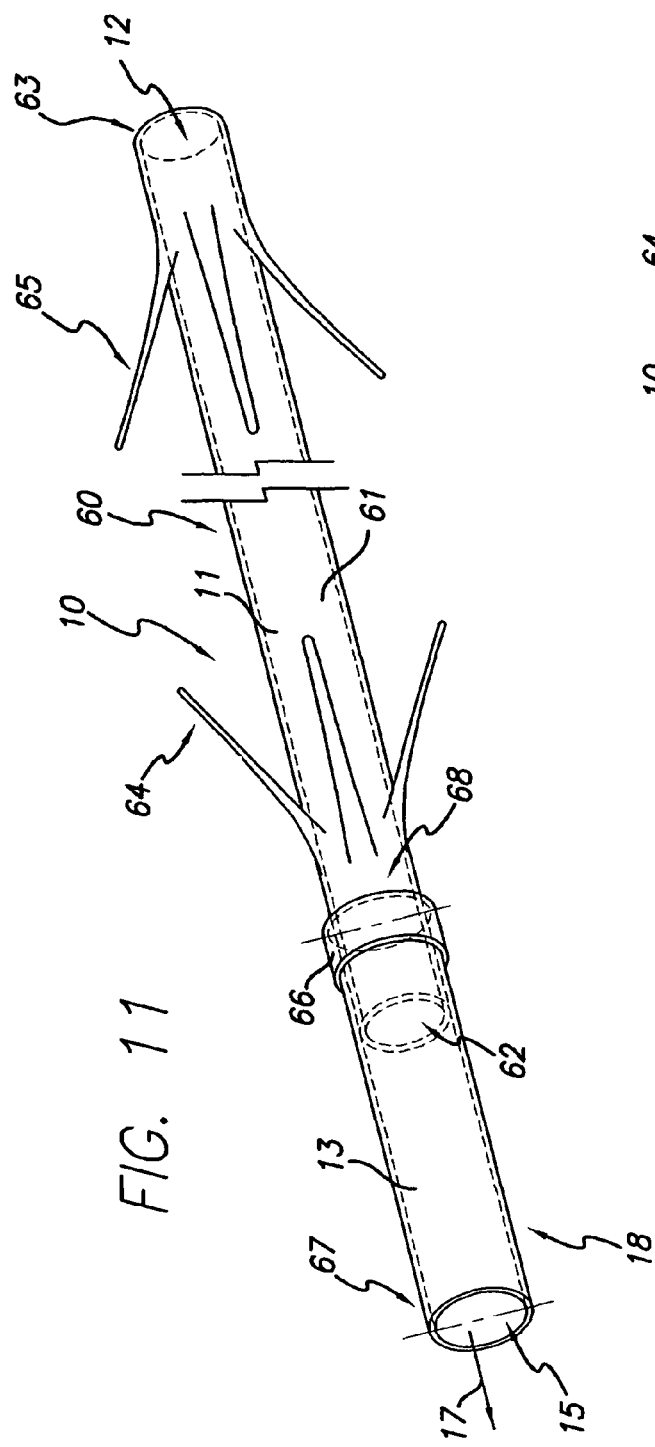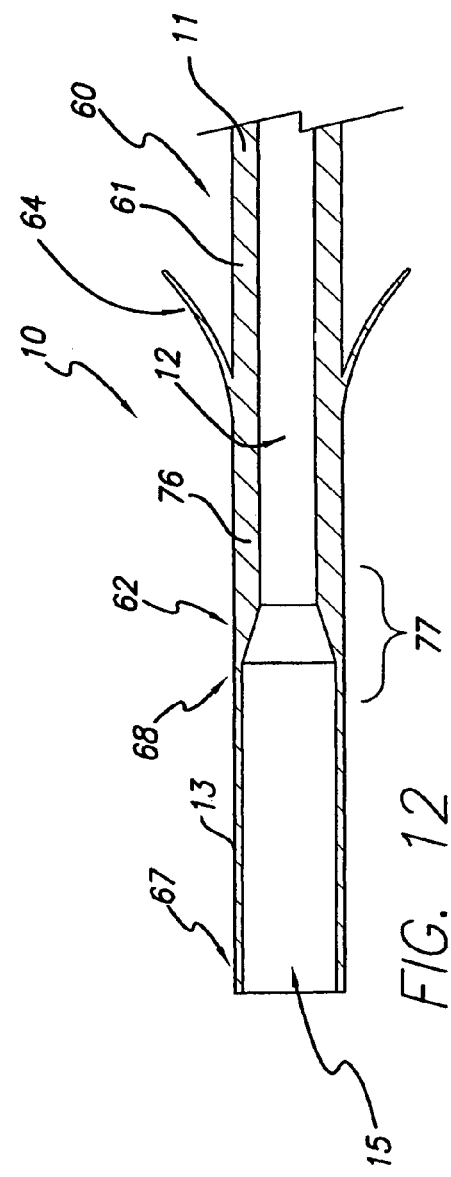

PROSTHESIS HAVING A SLEEVE VALVE

TECHNICAL FIELD

This invention relates generally to medical devices, and in particular, to an indwelling valved prosthesis.

BACKGROUND OF THE INVENTION

Anti-reflux esophageal prosthesis or stents are typically placed in the lower esophagus and through the lower esophageal sphincter to maintain the patency thereof due to the presence of a cancerous tumor commonly found in the vicinity thereof. The cancerous tumor growth typically impinges the flow of food and fluids through the esophagus. Lower esophageal cancer in the United States presently occurs at the rate of approximately 12,000 patients per year. The incidence in the United States is approximately 5.1 per 100,000 people, and is rising, particularly in white male patients. Esophageal prosthesis or stents are typically utilized in these cancerous patients. However, these devices are not FDA approved for benign tumors which also cause blockage or partial stenosis of the esophagus. Esophageal prosthesis or stents are utilized in Europe and other countries for benign tumor conditions, but are not being utilized in the United States at this time.

A problem with esophageal prosthesis or stents is that fluid from the stomach flows into the mouth of the patient when in a prone position. In an attempt to solve this problem, a number of esophageal prosthesis or stents utilize a one-way valve such as a duck-bill or reed-type valve in which food or fluid from the esophagus flows into the stomach in only an antegrade or forward direction. However, these one-way anti-reflux prosthesis or stents present certain problems. For example, when the patient wants to belch or vomit, he/she is prevented from doing so because the one-way valve prevents backward flow in the retrograde direction. Such a condition is not only painful to the patient, but can also lead to more complicated medical conditions.

There are other anatomical sites, such as the biliary tree or genitourinary system, in which a prosthesis may be placed to maintain an open lumen for passage of bodily fluids. Such prosthesis may create the risk of undesirable retrograde flow and/or migration of pathogenic organisms, which could lead to infection or other problems, such as obstruction of the stent. When a drainage stent or catheter is placed across a sphincter or natural stricture at the opening to a bodily passage, the sphincter or stricture cannot fulfill its normal function of restricting retrograde flow or migration. What is needed is a prosthesis and one-way valve that can effectively regulate antegrade and retrograde flow in response to the normal flow rates and pressures that exist across the site in which the prosthesis is placed.

BRIEF SUMMARY OF THE INVENTION

The foregoing problems are solved and a technical advance is achieved in an illustrative prosthesis having a sleeve which permits antegrade flow under a first pressure through the sleeve, and collapses in response to a second flow or pressure that is greater than the first flow or pressure.

In one aspect of the invention, the prosthesis comprises an anti-reflux esophageal prosthesis in which a sleeve extending from a tubular frame thereof inverts through the passage of the tubular frame and allows stomach gas or vomit to flow in a retrograde direction when the pressure in the stomach exceeds a given level (a third pressure higher than the second pressure). In the antegrade or downward position, the sleeve collapses and prevents the reflux of stomach gas and fluid from flowing through the esophagus and into the mouth of the patient. The collapsible sleeve functions as a one-way valve and allows the patient to ingest or pass liquid and food therethrough and into the stomach. In addition, the tubular frame of this advantageous anti-reflux esophageal prosthesis maintains the patency of the lower esophagus and sphincter, particularly when, for example, a cancerous tumor would otherwise impede fluid flow through the esophagus.

In another advantageous aspect of the present invention, the tubular frame of the anti-reflux esophageal prosthesis includes a plurality of self-expanding zig-zag stents. The compressed stents, along with the sleeve, are positioned in a delivery catheter that is orally passed through the esophagus and lower sphincter. The prosthesis is then deployed from the delivery catheter with, for example, a dilator or pusher catheter that is inserted in and/or through the lumen of the delivery catheter. Once deployed, the self-expanding stents readily expand to engage and maintain the esophagus and lower sphincter in a patent condition.

The self-expanding stents of the tubular frame are also advantageously flared at each end of the tubular frame to prevent antegrade and retrograde migration of the expanded prosthesis. To further prevent migration of the zig-zag stents with respect to each other, a filament is circumferentially positioned through closed eyelets at the bends of adjacent zig-zag stents. The filaments are also utilized advantageously to control the radial expansion and the flared configuration of the stents positioned at the ends of the tubular frame.

The pressure needed to collapse or invert the one-way valvular sleeve is a function of the sleeve material, its wall thickness, and length extending from the distal end of the tubular frame. Depending on the anatomical size of the human or veterinary patient, the sleeve can extend from the end of the frame for a length in a range of from 0.0 to 20 cm, and preferably in a range of 5 to 15 cm; and more preferably in a length of approximately 10 cm for a human patient or 8 cm for a veterinary patient, as experimentally derived therefor. The sleeve material also advantageously includes a material of polyurethane, silicone, polyamides, other urethanes or any biocompatible material that is flexible and acid resistant. The sleeve material, at the portion covering the frame itself, can have an advantageous thickness of 0.005" through 0.01". The sleeve extending from an end of the frame comprises a material having a thickness in a range of 0.0015" to and including 0.01". Advantageously, the length of the sleeve is made long enough so that it can be readily shortened to accommodate individual anatomical situations.

In yet another aspect of the invention, the sleeve is configured to reduce the tendency of it to invert through the tubular frame during episodes of increased gastric pressure (third pressure), such as belching, where it is not necessarily important physiologically that inversion take place. Accordingly, a portion of the sleeve may be modified to make it more difficult to invert. One such modification is to widen the sleeve toward the first end thereof (i.e., the end of the sleeve distanced away from the tubular frame), such that the sleeve is tapered or bell-shaped. The wider first end would be less likely to invert back through the narrower tubular frame. A second modification is to add a stiffened region, such as a ring, about the first end so as to inhibit the sleeve from inverting back through tubular frame in response to a third gastric pressure, such as belching, that is higher than the second pressure acting on the valve to keep it closed in the absence of incoming flow (first pressure). The intent is limit or prevent inversion when the third pressure is not sufficiently high to warrant an inversion that is necessary for patient health or comfort, especially given that the patient must re-invert the sleeve by swallowing liquid following each such episode. The ring or stiffened region of the sleeve can comprise a rolled first end of the sleeve, a thickened edge of sleeve material, or one or more rings or similar elements affixed to the sleeve material. The sleeve can be configured such that it closes above or below the stiffened region or ring.

In another aspect of the invention, the collapsible sleeve is attached to a proximal end of the tubular frame, such that the sleeve extends distally through the tubular frame.

In another aspect of the invention, the collapsible sleeve is attached to a tubular drainage stent, such as a biliary stent, to advantageously prevent reflux of intestinal contents and the associated bacteria into the passage of the stent. These bacteria are known to promote the formation of a biofilm that can lead to occlusion of the stent. With the stent placed in the biliary tree for maintaining patency of the bile or pancreatic duct and the Papilla of Vater, the sleeve extends down into the duodenum to provide a one-way valve for the flow of bile. When bile is not being secreted, the sleeve advantageously collapses to prevent backflow of material from the duodenum, a situation which might otherwise occur in a biliary stent without a closure means. Tubular drainage stents for placement in the ureters or urethra can include either a sleeve extending from one end to permit urine flow but prevent retrograde flow or pathogen migration toward the kidneys or bladder, or the sleeve may be located completely within the lumen of the drainage stent with one end of the sleeve being bonded or otherwise attached to the inner walls of the lumen.

In yet another aspect of the present invention, the stent includes first opening and a second opening configured for allowing fluid flow from the passage to the lumen in the first direction.

BRIEF DESCRIPTION OF SEVERAL VIEWS OF THE DRAWINGS

FIG. 1 depicts a pictorial view of an illustrative embodiment of a pressure sensitive anti-reflux esophageal prosthesis of the present invention;

FIG. 2 depicts an enlarged cross-sectional view of a sleeve about a cylindrical wire of a flared stent of the esophageal prosthesis taken along line 2-2 of FIG. 1;

FIG. 8 depicts an in-vitro barrier reflux curve for an anti-reflux esophageal prosthesis of the present invention;

FIG. 11 depicts a pictorial view of an embodiment of a tubular drainage prosthesis of the present invention;

FIG. 12 depicts a cross-sectional view of a second embodiment of a tubular drainage prosthesis;

DETAILED DESCRIPTION OF THE INVENTION

Figure 3:
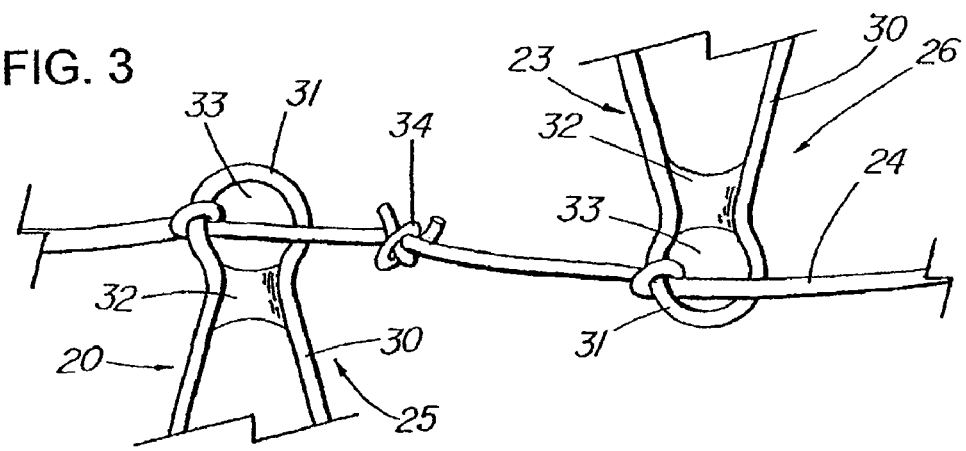
FIG. 3 depicts an enlarged partially sectioned view of the adjacent ends of interconnected stents of the prosthesis of FIG. 1.

FIGS. 1-14 depict exemplary prostheses of the present invention comprising a tubular member 11 with a passage 12 therethrough, and a thin, flexible sleeve 13 extending from the tubular member 11. The sleeve 13, which also has a passage 15 therethrough, is configured to allow the flow of liquid or other materials moving under a first pressure until the flow and pressure are lessened to where they are exceeded by a second, back pressure of the drainage environment, at which time the sleeve 13 collapses to prevent the ingress of fluids of materials into the tubular member.

FIG. 1 depicts a pictorial view of an illustrative, preferred embodiment of pressure sensitive anti-reflux esophageal prosthesis 10 of the present invention. The prosthesis includes a tubular frame 11 of a plurality 19 of self-expanding, zig-zag wire stents 20, 21, and 23 covered by a polyurethane sleeve 13 that is disposed around and extends along the entire length 27 of the tubular frame. The sleeve also extends from distal end 14 of the self-expanding tubular frame and has a lumen 15 extending longitudinally therethrough. Lumen 15 of the sleeve also communicates with passage 12 of the tubular frame. When the prosthesis is positioned in the lower esophagus and through the lower sphincter of a patient, lumen 15 in the lower portion 28 of the sleeve collapses upon itself due to wetting by gastric juices, fluid or saliva flowing therethrough from the esophagus in a first direction 17. As a result, sleeve 13 is in a collapsed position and acts as a one-way valve into the stomach, thereby preventing the reflux of gastric fluid from flowing in a retrograde manner, referred to herein as the second direction 18, through the prosthesis and esophagus and into the mouth of the patient. However, fluid may readily flow in the opposite (first) direction 17 from the esophagus and through the one-way valve sleeve into the patient's stomach.

Tubular frame 11 includes plurality 19 of self-expanding stents 20, 21, and 23 that are interconnected circumferentially by filament 24 about adjacent ends 25 and 26 of the stents. In this illustrative embodiment, the tubular frame includes four self-expanding, zig-zag wire metal stents of the Gianturco type as described in U.S. Pat. No. 4,580,568, which is incorporated by reference herein. It should be noted that the illustrative stent configuration is merely exemplary, and it is contemplated that other stents and stent configurations may be substituted for the illustrative stent frame.

The tubular frame includes first and second flared stents 20 and 21 positioned at distal and proximal ends 14 and 22, with first and second cylindrical stents 23 positioned therebetween. By way of example, first and second flared stents 20 and 21 have a minimum diameter of 18 mm and a flared diameter of approximately 25 mm. These diameters are nominal diameters for the stents and can be customized to meet the particular demands of any human or veterinary patient. The diameter of the flared end is maintained by end filament 29. The minimum diameter of the flared stents along with the nominal diameter of the cylindrical stents is maintained by interconnecting filaments 24. The interconnecting and end filaments 24 and 29 are, for example, 3/0 diameter mononylon suture material. The first and second flared stents 20 and 21 are positioned below and above the lower esophageal sphincter and prevent the migration of the prosthesis in either the antegrade or retrograde direction with respect to the esophagus. The flared proximal stent, along with the cylindrical stents 23, expand against any tumor that is in the region of the lower esophagus and maintains the patency of the lower esophageal lumen.

Flared stents 20 and 21 are, for example, are formed from commercially available Series 304 stainless steel cylindrical wire having a diameter of approximately 0.015". The wire is formed into a zig-zag pattern of which the ends are joined together using, for example, a metal sleeve and soldered together using silver/tin solder. However, other ways of forming a closed zig-zag configuration that at least resembles a partially tubular shape is contemplated. The flared or maximum diameter of the flared stents is approximately 25 mm with the minimum diameter at approximately 18 mm. Interconnecting cylindrical stents 23 are also formed from the same cylindrical wire and have a nominal diameter of approximately 18 mm, matching that of the minimum diameter of the flared stents. The length of the individual stents is approximately 2 cm. The overall length of the tubular frame can range from 8 to 14 cm in 2 cm increments. These 2 cm increments are typically provided by increasing the number of interconnecting cylindrical stents 23.

Sleeve 13 preferably comprises a polyurethane material or other liquid impermeable material that will not degrade in the presence of fluids or other gastric materials that it may come into contact with. The sleeve is disposed around, and extends at least partially around, tubular frame 11. Preferably, the sleeve extends the entire length of the frame and extends longitudinally from the distal end 14 of the tubular frame. The length of the sleeve material extending from the distal end of the tubular frame can range from 0 through 20 cm, preferably 5 to 15 cm, and more preferably from 7-10 cm. The length of the sleeve material can also be individually customized by the physician depending on the anatomy of the patient. Experimental data has indicated that dogs typically utilize a 7 cm length of sleeve material. Human patients are expected to utilize a sleeve length of 8 or 9 cm. However, and as noted above, the length of the sleeve can be modified by the physician to meet the particular anatomy of the patient.

The wall thickness of the sleeve material disposed around the tubular frame is approximately 0.006-0.01" thick. The thickness of the sleeve material along lower portion 28 of the sleeve may be thinner, e.g., approximately 0.002" thick; however, a thicker sleeve, such as 0.0095", may advantageously reduce the tendency of the sleeve to invert at back pressures (e.g., belching) below that which are deemed necessary for patient relief. The sleeve material preferably includes a medical grade polyurethane material, although silicone, nylon, polyamides such as other urethanes, or other biocompatible materials that are flexible and acid resistant are also suitable materials. In the particular embodiment illustrated herein, the sleeve material is a medical grade polyurethane material grade EG-80A material commercially known as TECOFLEX® polyurethane material from Thermedics, Inc., Woburn, Mass.

FIG. 2 depicts an enlarged sectioned end view, taken along line 2-2 of FIG. 1, of sleeve 13 about cylindrical wire 30 of flared stent 20. With respect to the embodiment shown in the drawing, the thickness of the sleeve material is approximately 0.006", whereas the thickness of the sleeve material along lower or distal portion 28 thereof is preferably and approximately 0.002". The thickness of sleeve material above distal portion 28 ranges from 0.005" through 0.01". Experimental data has indicated that the sleeve material along distal portion 28 will still collapse at a 0.01" wall thickness so as to effectively form a one-way valve. However, closure of the one-way valve sleeve material is most reliable at or below 0.004", since closure of sleeves with a thickness above this dimension may not occur each time on a guaranteed basis. However, if a desired goal is to limit the tendency of the sleeve to invert through the tubular frame 11, a thicker sleeve (0.004-0.01") may be desired. A thickness of the sleeve wall material below 0.0015" may present a problem of tearing, particularly when inserting the prosthesis into a delivery catheter.

FIG. 3 depicts an enlarged partially sectioned view of adjacent ends 25 and 26 of interconnected stents 20 and 23 of FIG. 1. Bends 31 of cylindrical wire 30 are formed into a keyhole configuration with silver solder 32 interconnecting the wire arms, thereby forming an aperture or eyelet 33. Interconnecting filament 24 is positioned through each eyelet and wound around at least once to aid in fixing the diameter of the expandable stents. One interconnecting or end filament is used at the end of each stent and tied at the loose ends with suture knot 34.

Figure 4:
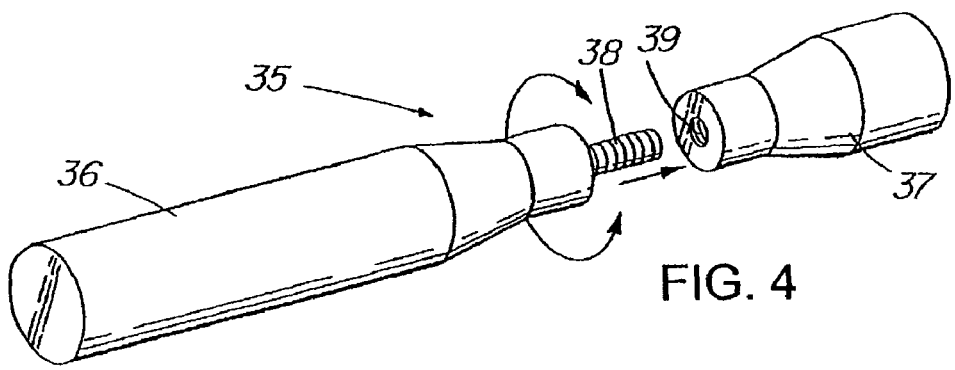
FIG. 4 depicts a two piece mandril that is used to apply the sleeve material to the prosthesis of FIG. 1.

FIG. 4 depicts a two piece mandril 35 that is used to apply sleeve material 13 to the prosthesis of FIG. 1. The mandril includes sleeve portion 36 and upper frame portion 37, which are interconnectable with, for example, threaded rod 38 and internally threaded channel 39. In use, the tubular frame including the plurality of self-expanding wire stents are positioned end-to-end and interconnected using interconnecting filament 24. The end filament is also positioned through the eyelets of the flared stents to control the maximum diameter thereof. The mandril has a minimum inner diameter matching that of the inside diameter of the inner stents and a flared diameter matching that of the flared stents. Extending from the ends of the flared portions, the mandril assumes the inner diameter of the one-way valve sleeve material. The assembled tubular frame is positioned between the upper frame portion of the sleeve portion of the mandril. The two portions of the mandril are then interconnected, thereby filling up the passage of the tubular frame. The tubular frame is then dipped into a slurry material of polyurethane to form an initial 0.004" thickness over the entire length of the tubular frame. The mandril and covered tubular frame are then dipped in the slurry material at least one additional time to form the desired thickness of the sleeve material over mandril sleeve portion 36. After the slurry material cures, the two portions of the mandril are disconnected to form the anti-reflux esophageal prosthesis.

Figure 5:
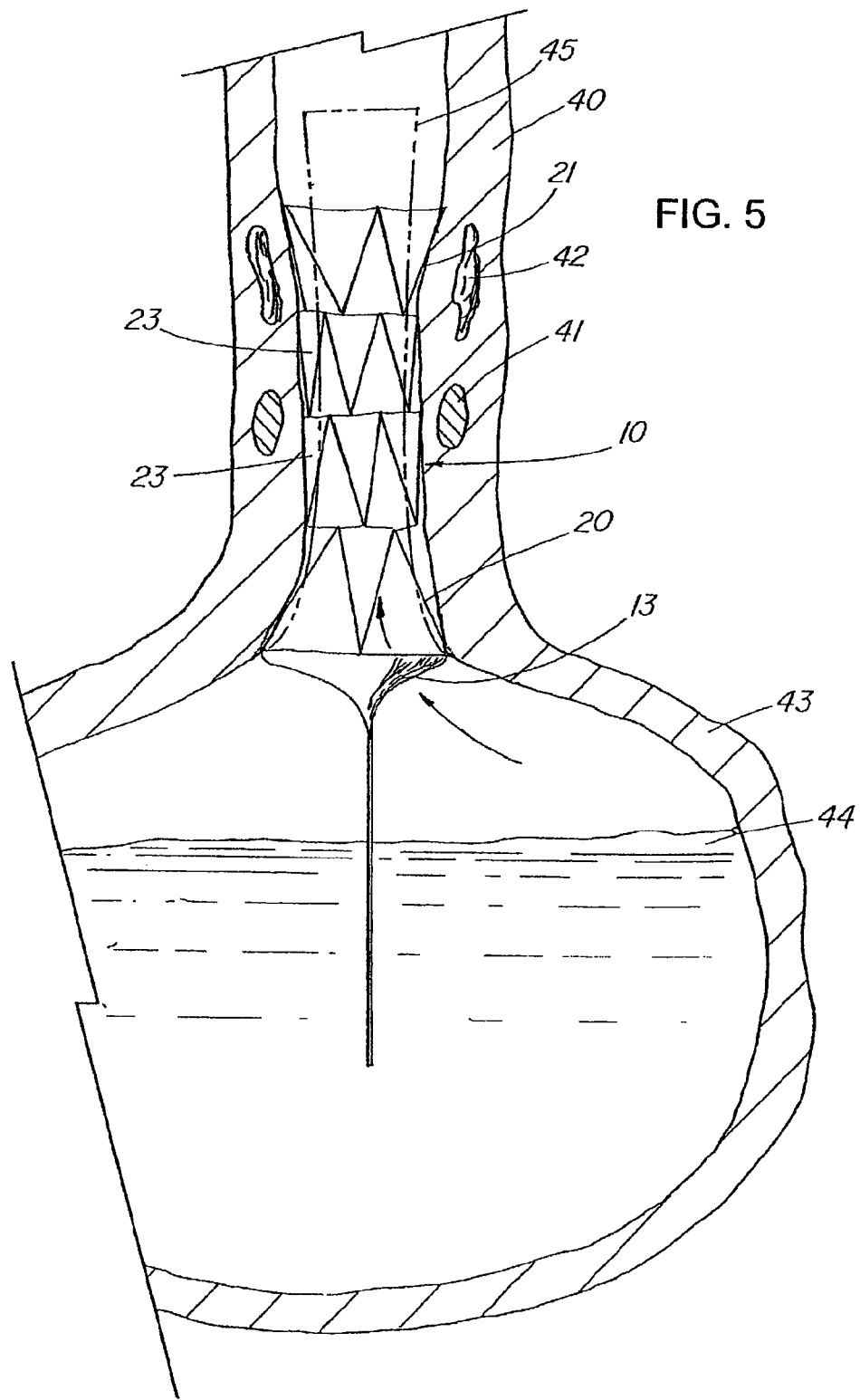
FIG. 5 depicts the esophageal prosthesis of FIG. 1 deployed in the lower esophagus of a patient, and in particular, through the lower esophageal sphincter and a cancerous tumor.

FIG. 5 depicts esophageal prosthesis 10 deployed in lower esophagus 40, and, in particular, through lower esophageal sphincter 41 and cancerous tumor 42. Distal flared stent 20 typically extends into the stomach along with sleeve 13. Flared stent 21 is positioned proximal to the sphincter and tumor, whereas the interconnected cylindrical stents are typically positioned through the sphincter and tumor. The flared stents 20 and 21 prevent the migration of the prosthesis within the esophagus. The lower or distal portion 28 of sleeve 13 extends into stomach 43. The lumen of the lower sleeve portion readily collapses when in contact with any external fluid applied thereto. However, any liquid or food is readily passed in an antegrade direction through the esophageal stent and into the stomach. As a result, one-way valve sleeve 13 opens to provide flow in the antegrade direction. Conversely, any fluids or food material 44 are prevented from flowing into the retrograde direction due to the collapsed lumen of sleeve 13. However, when the pressure of the gas or fluid in the stomach builds so as to cause the patient to belch or vomit, sleeve 13 will invert and extend in an antegrade direction through the lumen of the tubular frame as shown by phantom lines 45. In this position, gastric fluid and matter flows in the retrograde direction to relieve the patient. The length of distal portion 28 of the sleeve and the thickness thereof control the pressure at which the distal portion of the sleeve inverts through the tubular frame.

Self-expanding esophageal prosthesis are increasingly being used for palliation of malignant dysphagia. However, these devices can predispose a patient to significant gastroesophageal reflux, including risk of aspiration, when deployed across the gastroesophageal junction. A study was performed to evaluate the anti-reflux efficacy of a esophageal prosthesis of the present invention to prevent reflux. A model EZS 21-8 from Wilson-Cook Inc., Salem, N.C. (16 mm diameter) was modified by extending its polyurethane covering 7 cm beyond its distal metal cage so as to form a "windsock" or collapsible sleeve. The pressure required to invert the windsock or collapsible sleeve into the tubular frame (reflux barrier) was determined by attaching the proximal end of the prosthesis to a hollow graduated tube and vertically inserting the stent under water until the windsock inverted. The pressure required to revert the windsock or collapsible lumen to its original one-way position was subsequently determined by pouring water into the lumen of the prosthesis. In-vivo evaluation was done in two esophagostomized dogs (male—18 kg, female—16 kg). Prosthesis insertion, positioning, and removal were accomplished by standard endoscopic and fluoroscopic techniques. Two site ambulatory esophageal pH monitoring (Synectics Medical) was performed at 5 cm and 10 cm above the gastroesophageal function. Each dog was studied twice using the standard model EZS 201-8 prosthesis and twice using the modified prosthesis (mean recording time per session 18.7+/−1 SE and 17+/−3 hours respectively). The results indicated that the windsock modification posed no difficulty in mounting or deploying the prosthesis using a currently available delivery system. Resistance to antegrade flow was minimal as even a drop of water placed into the prosthesis easily passed through the windsock and both the dogs drank all the Ensure (4 cans per session) given to them irrespective of the type of prosthesis used. The pressure (cm of water) to overcome the reflux barrier was 15.7+/−0.3 SE and that to revert an inverted windsock or collapsible lumen was 0.4+/−0.03 SE. Results of the pH monitoring (mean+/−SE) are depicted in Table 1.

TABLE 1

|  | Standard Stent | | Anti-reflux Stent | |
| --- | --- | --- | --- | --- |
| Recording site (cm) above GEJ | 5 | 10 | 5 | 10 |
| Number of reflux episodes | 229 ± 25" | 56 ± 9@ | 9.7 ± 7* | 8 ± 5@ |
| Fraction time pH <4 (%) | 60 ± 5* | 7.6 ± 2@ | 0.7 ± 0.3* | 0.2 ± 0.1@ |

The conclusions reached in the experiment were that a modified self-expanding metal esophageal prosthesis is highly effective in preventing reflux. The ability of the windsock or collapsible lumen sleeve 13 to invert at higher pressure gradients can allow patients to belch or vomit. Reversion to anti-reflux position requires minimal pressure and can be achieved by a water swallow. The results of further studies are reflected in FIGS. 8-10.

Figure 6:
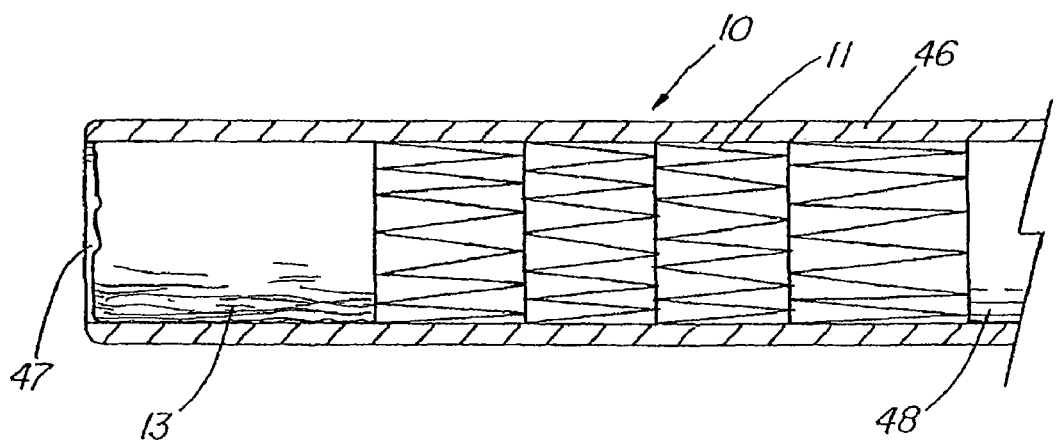
FIG. 6 depicts the anti-reflux esophageal prosthesis of FIG. 1 in a collapsed state in a delivery catheter.

FIG. 6 depicts the anti-reflux esophageal prosthesis 10 of FIG. 1 in a collapsed state in delivery catheter 46. Sleeve material 13 is positioned at the distal end of the delivery catheter. The prosthesis is drawn into the delivery catheter with a drawstring attached at the proximal end of the prosthesis. The drawstring and prosthesis are inserted through lumen 47 of the catheter by collapsing the tubular frame and then pulling the prosthesis into the distal end of the delivery catheter with the drawstring. To deploy the collapsed prosthesis from the delivery catheter, a pusher catheter 48 is positioned proximally in lumen 47 to engage the proximal end of the wire tubular frame 11.

Figure 7:
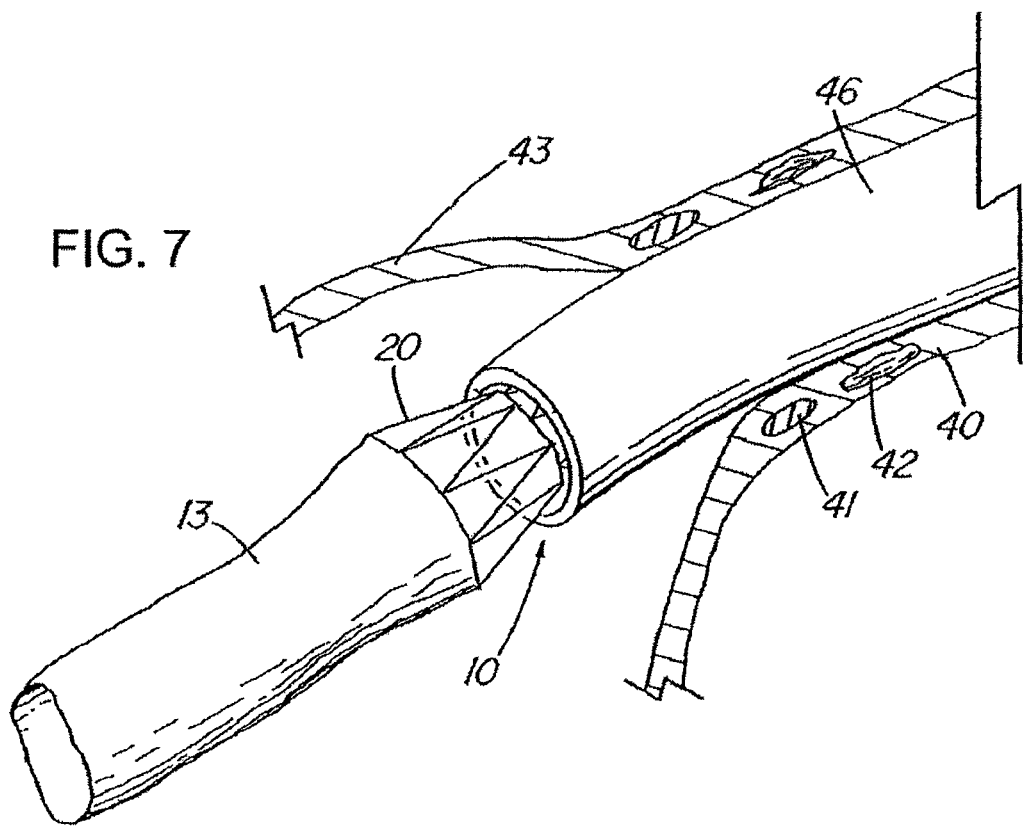
FIG. 7 depicts the delivery catheter of FIG. 6 positioned in the lower esophagus, sphincter, and tumor of a patient.

FIG. 7 depicts delivery catheter 46 of FIG. 6 positioned in lower esophagus 40 and sphincter 41 of a patient, and adjacent to tumor 42. The distal end of the delivery catheter extends into stomach 43. As shown, the pusher has been placed in the lumen of the delivery catheter and engages the proximal end of prosthesis 10. As shown, sleeve 13 and flared distal stent 20 have been deployed from the distal end of the catheter. After the sleeve and distal flared stent 20 of the prosthesis have been deployed, the delivery catheter is partially withdrawn so as to engage the flared stent with the neck of the stomach about sphincter 41. Once positioned, the delivery catheter is pulled back while maintaining the position of the pusher catheter therein so as to release the central cylindrical stents and proximal flared stent against the sphincter, tumor, and lower esophagus.

An in-vitro and in-vivo evaluation of a modified self-expandable metal esophageal stent with an anti-reflux mechanism of the present invention was performed on a number of dogs. The evaluation included four dogs, two of which were males at 14 and 18 kg and two females at 14 and 16 kg. An esophagostomy was utilized with the use of upper gastrointestinal endoscopy. The evaluation included the methods of ambulatory pH monitoring with the use of Synectics medical equipment at 5 and 10 cm with Gastrograph Inc. software. A liquid diet of Ensure at a pH of 6.5 was administered. The results of the employed methods are included in Table 2.

TABLE 2

|  | Standard Stent | Anti-Reflux Stent | P |
| --- | --- | --- | --- |
| Duration of pH Monitoring (hrs · mins) | 20.30 ± 1.6 | 21.38 ± 0.9 | ns |
| Oral Intake Ensure (ml) | 1007 ± 0.5 | 978 ± 0.4 | ns |

FIG. 8 depicts in-vitro reflux barrier curve 48 that illustrates the water column height in centimeters necessary to invert a given sleeve length extending from the distal end of the prosthesis. Rectangular median value boxes 49 indicate the median value of the water column height at the indicated sleeve lengths. The vertical bar 50 positioned on curve 48 with rectangular median value boxes 49 represent a standard deviation above and below the indicated median value. In addition, the number of reflux episodes was monitored at the distal and proximal ends of the prosthesis. With a standard prosthesis without a one way valve, 197 episodes of reflux were encountered in 250 attempts. At the proximal end of the standard tubular esphageal prosthesis, a total of 33 reflux episodes were noted with 50 attempts. Correspondingly, only 16 reflux episodes were noted out of 250 attempts at the distal end of an anti-reflux esophageal prosthesis of the present invention. At the proximal end of the anti-reflux esophageal stent only 8 episodes out of 50 attempts were noted. The number of reflux episodes longer than five minutes was also noted. In the standard prosthesis, 19.8 episodes were recorded for 25 attempts. This is in contrast to 0.3 episodes for an anti-reflux esophageal stent of the present invention. At the proximal end of the prosthesis, 2.3 episodes lasting longer than five minutes were noted with three attempts; whereas none were noted with the anti-reflux prosthesis. The longest reflux episodes were also noted at the distal and proximal ends of the standard and anti-reflux prosthesis. For the standard prosthesis, 107 episodes were noted out of approximately 130 attempts; whereas only 3.8 were noted for the anti-reflux prosthesis at the distal end thereof. At the proximal end of the prosthesis, 39 episodes were noted out of 45 for the standard prosthesis; whereas only 1.8 were noted for the anti-reflux prosthesis.

Figure 9:
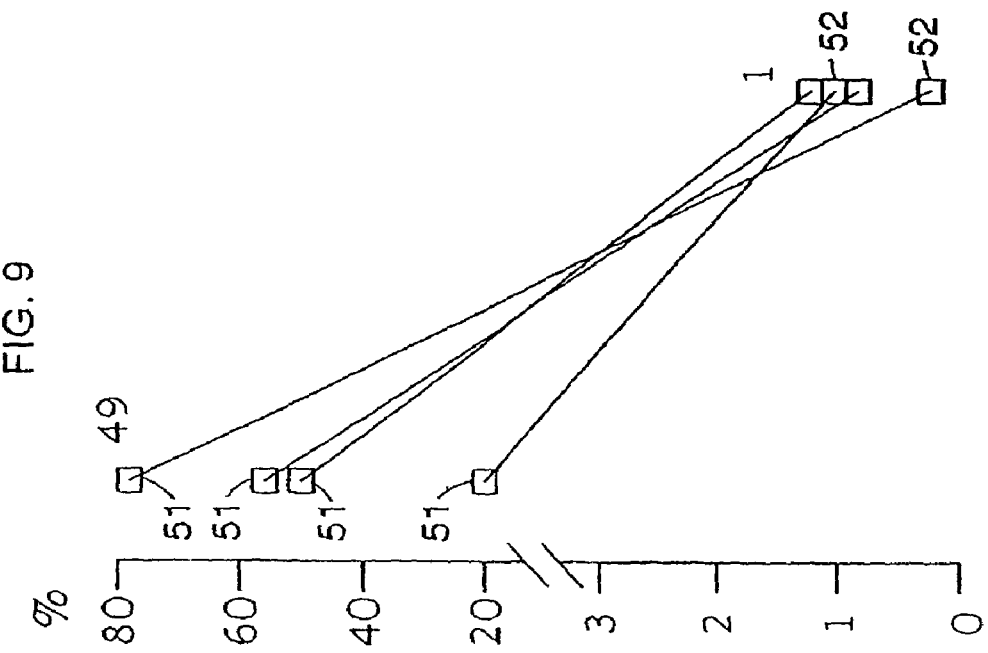

FIG. 9 depicts the fraction time percentages of which the esophagus was exposed to gastric juice with a pH less than 4. At the distal end of the prosthesis, the percentage of fraction time is indicated by boxes 51 for the four dogs at the distal end of the standard prosthesis. These percentage fraction times range from 20-80% with a median value of 49%. For the anti-reflux prosthesis, the percentage of fraction time ranges from 0.0 to approximately 1.5% with a median value of 1% as indicated by boxes 52. The p-values for these fraction times is 0.026.

Figure 10:
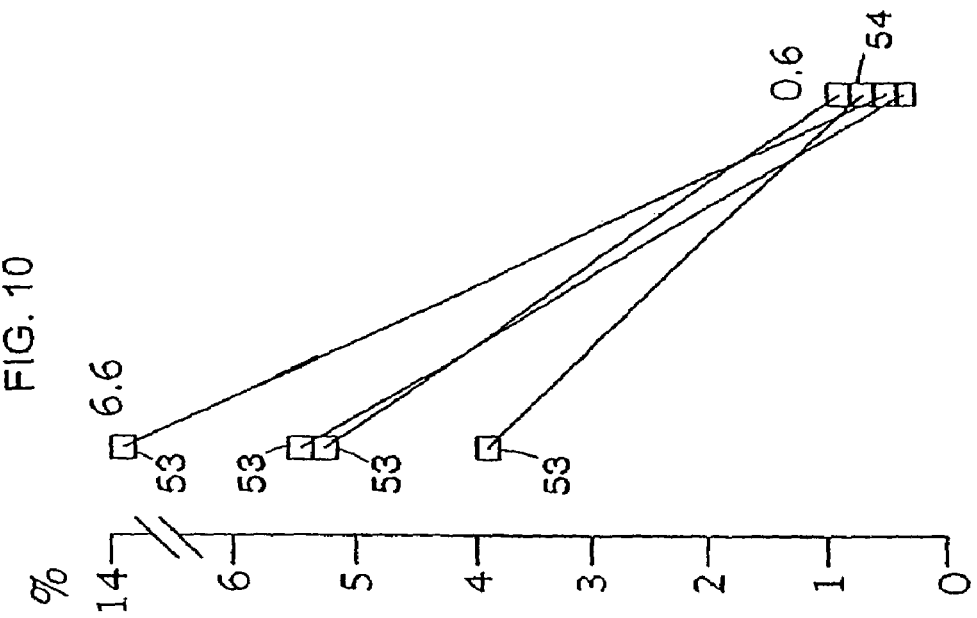
FIGS. 9 and 10 depict the percent of fraction time of standard and anti-reflux esophageal prosthesis utilized in an evaluation of the present invention.

FIG. 10 depicts the fraction time percentages at the proximal ends of the standard and anti-reflux prosthesis. Boxes 53 represent the percent fraction time for the standard prosthesis which ranges from approximately 4-14% with a median of 6.6%. Rectangular boxes 54 represent the percent fraction time for the anti-reflux prosthesis, which range from approximately 0.0 to 1.0%. These have a p-value of approximately 0.055.

The conclusions resulting from this in-vitro and in-vivo evaluation are as follows. The modified self-expanding metal esophageal stent of the present invention is highly effective in preventing gastro-esophageal reflux. The ability of the modification to invert at higher pressure gradients allows for belching and vomiting. Once inverted, reversion to the anti-reflux position of the prosthesis requires minimal pressure that can be achieved by a water swallow.

Figure 17:
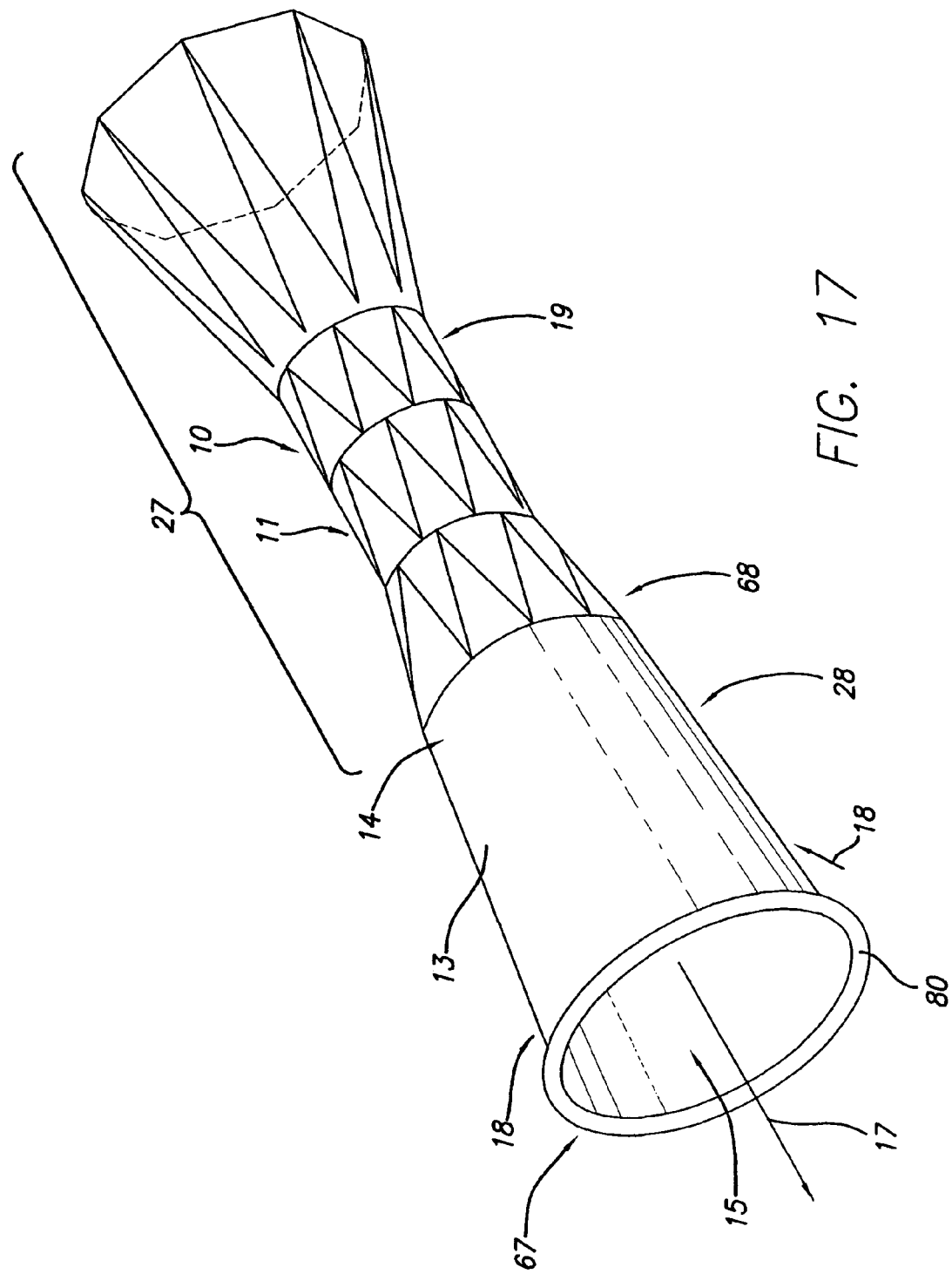
FIG. 17 depicts a pictorial view of second embodiment of a pressure sensitive anti-reflux esophageal prosthesis of the present invention.

A related esophageal embodiment of the present invention is depicted in FIG. 17, in which a portion of the collapsible sleeve 13 is adapted to be resistant to inversion through the tubular frame in response to a third pressure, such as belching. In the illustrative example, at least a portion of the sleeve is wider toward the first end 67 than it is at the second end 68 (the end of the collapsible portion at the junction with the end 14 of the tubular frame 11 comprising the plurality of expandable stents 19), such that the sleeve 13 is flared, tapered, conical or bell-shaped. In other words, the surface of the portion of the sleeve 13 extending between first end 67 and the second end 68 could be straight, convex, or concave, or any combination of these shapes, so long as the first end 67 is wider than the second end 68. In the illustrative embodiment, the width of the second end 68 is approximately 25 mm. From this point the sleeve diameter widens until it reaches approximately 31 mm at the first end 67. The wider, first end 67 helps prevent the collapsible sleeve 13 from inverting through the tubular frame. As explained above, inversion of the collapsible sleeve requires that the patient to subsequently take a drink of water to re-invert the sleeve back to the anti-reflux position.

A second modification of the embodiment of FIG. 17 intended to prevent the collapsible sleeve 13 from inverting into the frame 11 is a thickened or stiffening region 80, such as the illustrative ring at the first end 67 of the sleeve 13. More than one ring may be present, or the thickened region(s) 80 can comprise various non-annular configurations. The stiffening ring 80, which can comprise a rolled first end 67 of the sleeve, a thickened edge formed with additional sleeve material, or a ring of material that has been affixed to the sleeve, adds rigidity to the sleeve and decreases the likelihood that it will invert in situations during which it is not desirable or necessary for inversion to take place. The addition of either of these modifications may also permit the sleeve material to be thinned to produce a better seal against normal back pressure 18 of fluids. For example, while a sleeve 13 having a thickness of 0.004 or 0.005" collapses more readily, it can sometimes invert back through the stent at back pressures where inversion would not truly be necessary to relieve problematic gastric pressure or to vomit, thereby requiring that the patient drink a glass of liquid to re-invert the sleeve.

Inversion through the tubular frame 11 should be a relatively rare event, and in some patients, such as those having a Nissan Fundiplication, may not be necessary due to a greatly reduced ability to belch or vomit. To address the problem of inappropriate inversion, the sleeve may be thickened, e.g., to 0.0095" to make inversion through the frame more difficult. Although a thicker sleeve is more difficult to re-invert, it may not make an optimal valve. Thus, the ring 80 and/or distal enlargement of the sleeve 12 represent other ways to address the inversion problem. The illustrative modifications may also allow the sleeve to be made shorter (e.g., less than 8 cm) and still retain the desired valve characteristics.

It should be noted that the anti-inversion features depicted in FIG. 17 may be applied to other types of stents and to prostheses placed elsewhere in the body to serve as a valve. For example, the above-described anti-inversion features may be used on tubular drainage stents of the type described below.

Figure 18:
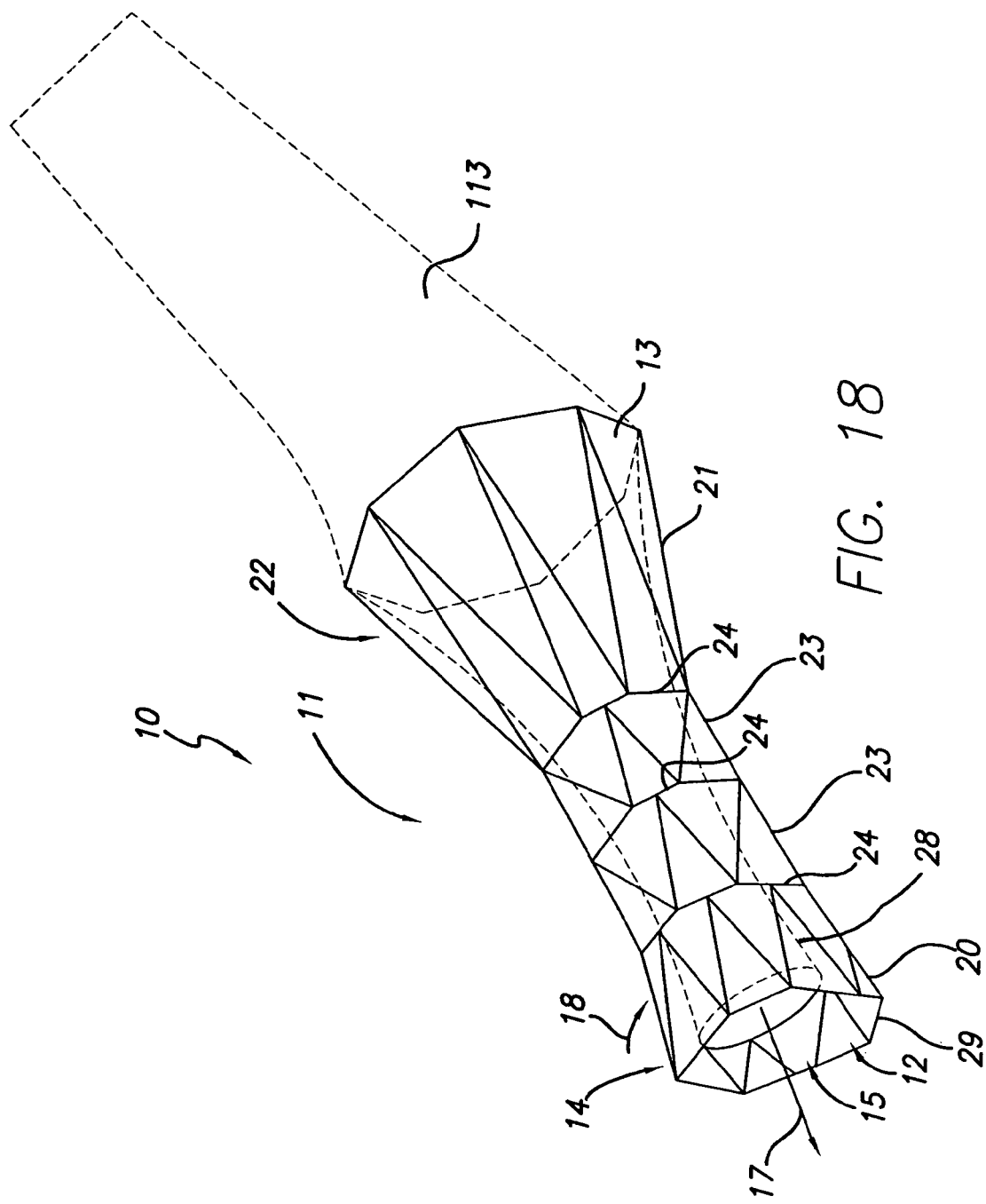
FIG. 18 depicts a pictorial view of a third embodiment of a pressure sensitive anti-reflux esophageal prosthesis of the present invention.
Figure 19:
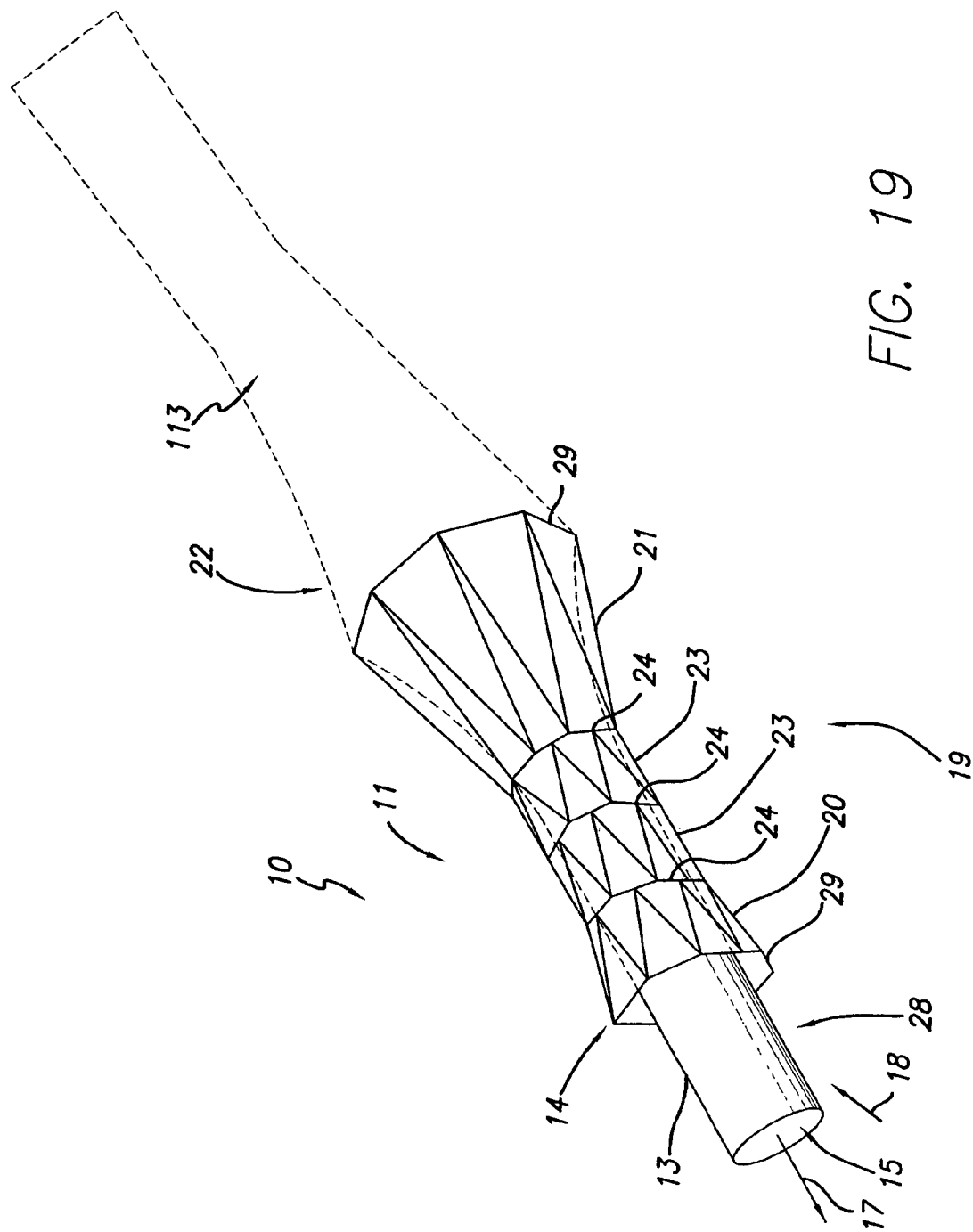
FIG. 19 depicts a pictorial view of a fourth embodiment of a pressure sensitive anti-reflux esophageal prosthesis of the present invention.

FIGS. 18-19 illustrate an embodiment of a pressure sensitive anti-reflux esophageal prosthesis 10 in which the collapsible sleeve 13 extends distally from the proximal end 22 of the tubular frame. As illustrated in FIGS. 18-19, the prosthesis includes a tubular frame 11 of a plurality 19 of self-expanding, zig-zag wire stents 20, 21, and 23. The tubular frame 11 includes a proximal end 22 and a distal end 14. A sleeve 13 is attached to the proximal end 22, rather than the distal end 14.

As illustrated in FIG. 18, the sleeve 13 extends distally through passage 12 of the tubular frame. In particular, the sleeve extends distally through a portion of the length of the passage 12. The sleeve 13 can be everted (shown as everted sleeve 113). The sleeve can also be provided in shorter or longer lengths. For example, the sleeve can be provided in lengths greater than, less than, or equal to the axial length of the tubular frame. The embodiment illustrated in FIG. 18 includes a sleeve that is shorter than the tubular frame.

The use of a sleeve having a shorter length than the tubular frame may be particularly well-suited for use with patients suffering from hiatial hernia. In patients with hiatal hernia there is often a compression of the esophagus at the esophageal junction adjacent the diaphragm. This compression in some circumstances can be severe enough to compress or pinch the sleeve valve, and possibly prevent it from everting. However, in the embodiment of FIG. 18, the sleeve is protected from such compression or pinching because the entire length of the sleeve is disposed within the tubular member, which traverses the problematic esophageal junction.

The embodiment illustrated in FIG. 19 includes a sleeve that is longer than the tubular frame 11. As shown, the sleeve 13 can be everted (shown as everted sleeve 113) to extend proximally from the proximal end 22 of the tubular frame. This allows a patient to vomit or belch when necessary, as described above. As described above with respect to previous embodiments, the patient can cause the sleeve to return to its normal first configuration by, for example, drinking water.

The prostheses 10 illustrated in FIGS. 18-19 can also be provided with the anti-inversion features depicted in FIG. 17. For example, the sleeve 13 can be provided with rings, a bell-shaped portion, portions of varying thickness or stiffness, and the like, as described in detail above.

In yet another embodiment of the present invention depicted in FIGS. 11-14, the prosthesis 10 and tubular member 11 comprise a tubular drainage stent 60 having a first end 62 for drainage into a duct, vessel, organ, etc., and a second end 63 that receives the fluid or other material that is moving under a first, antegrade pressure and direction 17. As generally defined, a tubular drainage stent (or tubular drainage catheter) is typically an elongate, closed tubular conduit (typically plastic or metal) that is placed within a bodily passage, such as the bile duct, pancreatic duct, urethra, etc. to facilitate the flow of fluids therethrough. It is typically non-expanding, unlike the wire or open-frame stents of FIGS. 1-10. It is commonly placed either to establish or maintain patency of the bodily passage or to drain an organ or fluid source, such as the gall bladder or urinary bladder. The tubular drainage stent may also include a retention means 64, 65 at one or more ends 62, 63, such as flaps, barbs, pigtail loops, etc. The tubular drainage stent 60 is attached to the collapsible sleeve 13, which acts as a one-way valve to prevent retrograde flow 18 therethrough. The first end 67 of the sleeve is maintained open when the fluid or material passing through the sleeve is exhibiting a pressure associated with normal antegrade flow 17. The first end 67 collapses shut when the antegrade flow 17 has ceased or lessened such that the second fluid pressure 18 occurring in the environment into which the fluid is drained becomes higher than the first pressure of the antegrade flow 17. In the illustrative biliary stent embodiment, bile is able to flow into the duodenum 71. However, the sleeve 13 closes in the absence of measurable flow 17, thus preventing the contents of the intestinal tract, which now have a second, higher pressure 18, from entering the passageway of the stent. The sleeve 13 is made of a biocompatible material that will not degrade when placed in the particular environment of the human body into which it is to be placed. Possible materials include expanded polytetrafluoroethylene (ePTFE), polyurethane, silicone, nylon, polyamides such as other urethanes, or other biocompatible materials. It is important that the sleeve material be selected appropriately. For example, in the illustrative embodiment, the sleeve is typically made of a 2-3 cm section of ePTFE, which is much more resistant to caustic bile than would be a sleeve of polyurethane. The ePTFE tube is extruded into a thin wall tube having sufficient flexibility to collapse and seal against the ingress of fluid, while having sufficient integrity to resist tearing. The normal range of sleeve thickness for the illustrative embodiment is 0.001 to 0.01 in., with a more preferred thickness of 0.002 to 0.005 in (e.g., 0.0025). The second end 68 of the sleeve is attached about the first end 62 of a biliary stent 60, such as a ST-2 SOEHENDRA TANNENBAUM® stent, a COTTON-LEUNG® stent or a COTTON-HUIBREGTSE® stent (Wilson-Cook Medical Inc., Winston-Salem, N.C.), by an attachment means 66, such as an illustrative crimped metal band. This band 66 can also be made radiopaque so as to serve as a fluoroscopic marker. Other methods of attachment could include, suture binding, selected medical grade adhesives, or thermal bonding, if appropriate for both the sleeve and stent polymers.

An alternative method of forming the sleeve for a tubular drainage stent 60 is depicted in FIG. 12. Rather than attaching a separately extruded or preformed sleeve 13 to the tubular member 11, the wall of the tubular member, which is made of polyethylene in this embodiment, is thinned out distally from the first end 62 of the tubular drainage stent 60, such that the sleeve 13 is integral with the tubular member 11. A transition zone 77 exists between the first end tubular drainage stent 60 and the second end 68 of the sleeve 13, beyond which the sleeve 13 becomes sufficiently thin to collapse into a closed position in the absence of antegrade flow 17, such as bile.

Figure 13:
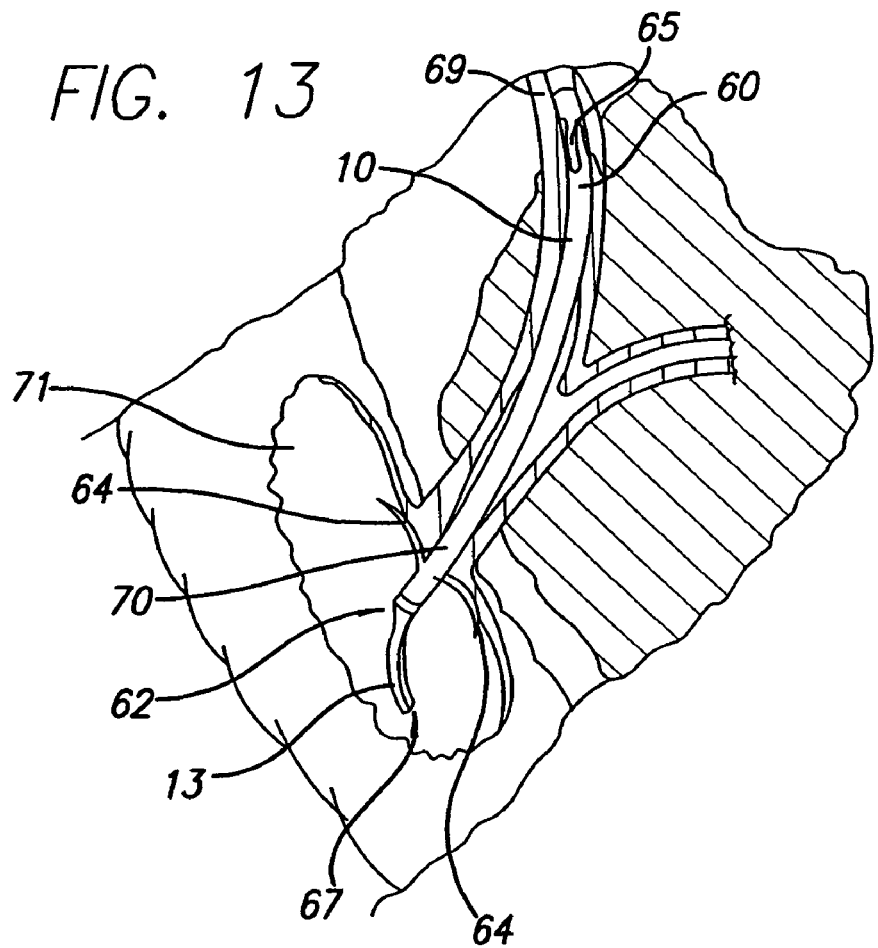
FIG. 13 depicts the prosthesis of FIG. 11 positioned in the common bile duct of a patient.

FIG. 13 depicts how the illustrative embodiment is used within the common bile duct 69 to permit the drainage of bile across the Papilla of Vater 70 and into the duodenum 71. The biliary stent 60 is positioned in the normal manner inside the common bile duct 69 with the first end 62 of the stent extending outside of the duct and Papilla of Vater 70. The first retention means 64 abuts the opening of the sphincter to prevent ingress of the stent 60 into the duct while the second retention means 65, located about the second end 63, is positioned well inside the duct to prevent the stent 60 from migrating outward. The sleeve 13 lies completely within the duodenum, where it acts as a one-way valve to prevent intestinal contents from entering the biliary stent 60. Unlike the embodiment of FIG. 1, the sleeve 13 is not designed to invert back through the tubular member 13 in the presence of a third, significantly higher pressure, a situation which is normally not found inside the duodenum, or even clinically necessary as with the esophageal embodiment where belching or vomiting make such a capability desirous. Accordingly, it may be desirable to incorporate one or more of the anti-inversion features depicted in FIG. 17.

Figure 14:
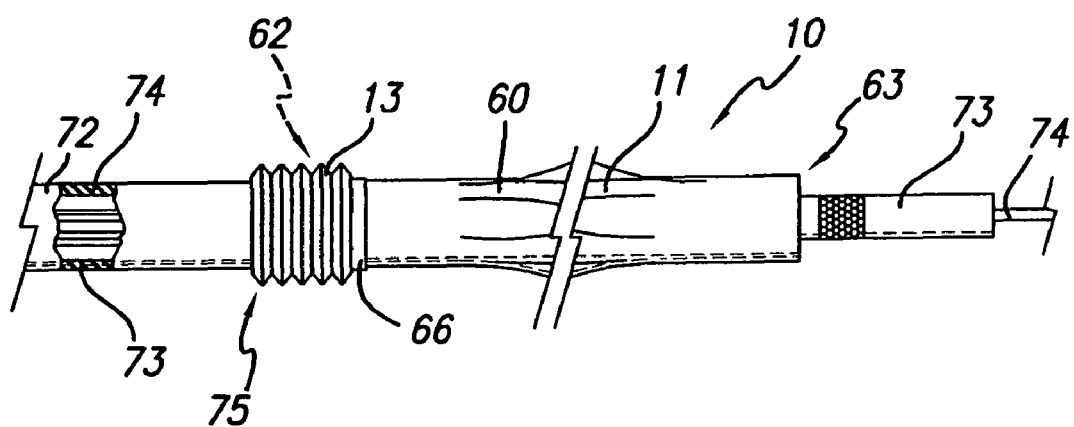
FIG. 14 depicts a side view of the prosthesis of FIG. 11 mounted on a delivery system.

Placement of the embodiments of FIGS. 11-12 can be accomplished by a system such as that depicted in FIG. 14. The biliary stent 60 is mounted on a guiding catheter 73 which is fed over a standard biliary exchange wire guide 74 into the bile duct. To deploy the stent from over the guiding catheter 73, a pusher element 72 is used with the distal end 75 of the pusher contacting the first end 62 of stent 60 and urging it forward until deployment occurs. The sleeve 13 is normally folded in accordion fashion prior to deployment, whereby it resumes its elongated configuration once the prosthesis 10 has been properly positioned.

Figure 15:
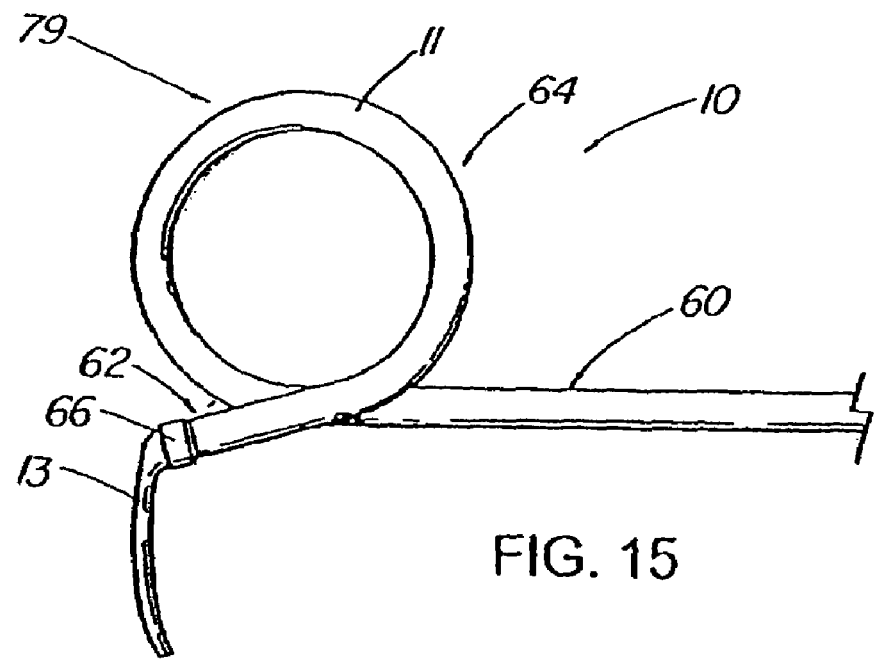
FIG. 15 depicts a side view of one end of a valved prosthesis that includes a pigtail configuration.

FIG. 15 depicts a prosthesis 10 comprising a tubular drainage stent 60 that is configured for placement in the urinary system, such as within the ureter between the kidney and the bladder. The sleeve 13 is attached to the first end 62 of the tubular drainage stent 60, which includes a first retention means 64 that comprises a pigtail configuration 79. In a ureteral stent, the pigtail 79 would be placed within the bladder to prevent migration of the stent. Optionally, a pigtail configuration 79 can be used to anchor the second end of the stent (not shown), typically within the ureteropelvic junction. The pigtail configuration is exemplary of a large variety of well know pigtail ureteral and urethral stents.

Figure 16:
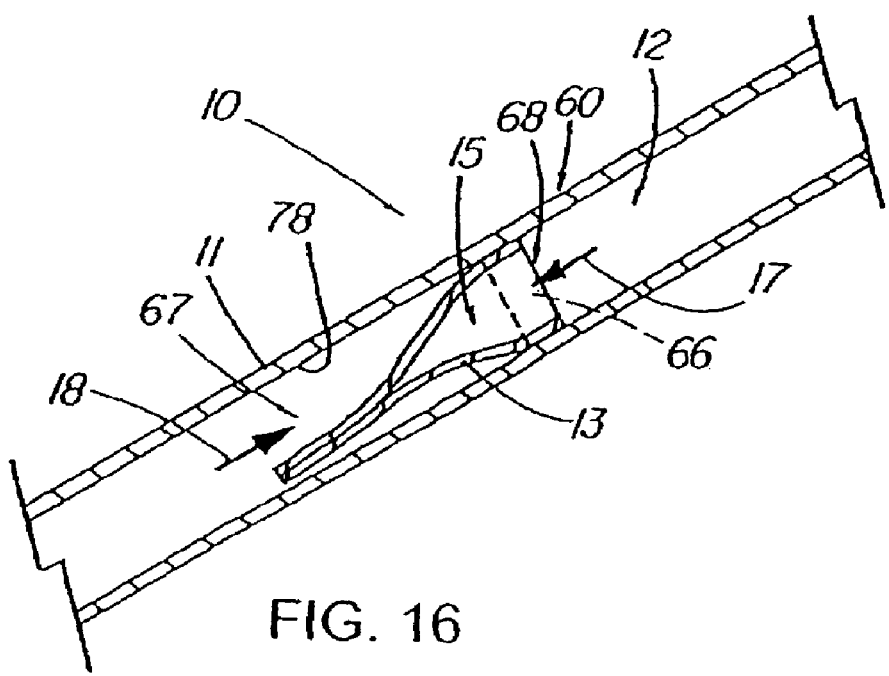
FIG. 16 depicts a laterally sectioned view of a valved prosthesis in which the sleeve is affixed with the lumen.

FIG. 16 depicts a tubular drainage stent 60 in which the first end 68 of the sleeve 13 is affixed completely within the lumen 12 of the stent 60, the attachment 66 comprising a well-known means such as thermal bonding, adhesive, or a ring of material that can affix the sleeve 13 material to the inner walls 78 of the stent 60. In the illustrative embodiment, the sleeve 13 resides completely within the lumen 12 such that it does not extend beyond the end of the tubular drainage stent 12. This could have particular utility in a urethral stent to prevent migration of pathogenic organism though the stent and into the bladder, while still allowing the antegrade flow of urine 17. Having a sleeve 13 extending out of the urethra would normally be less acceptable from a clinical and patient's point of view.

Figure 20:
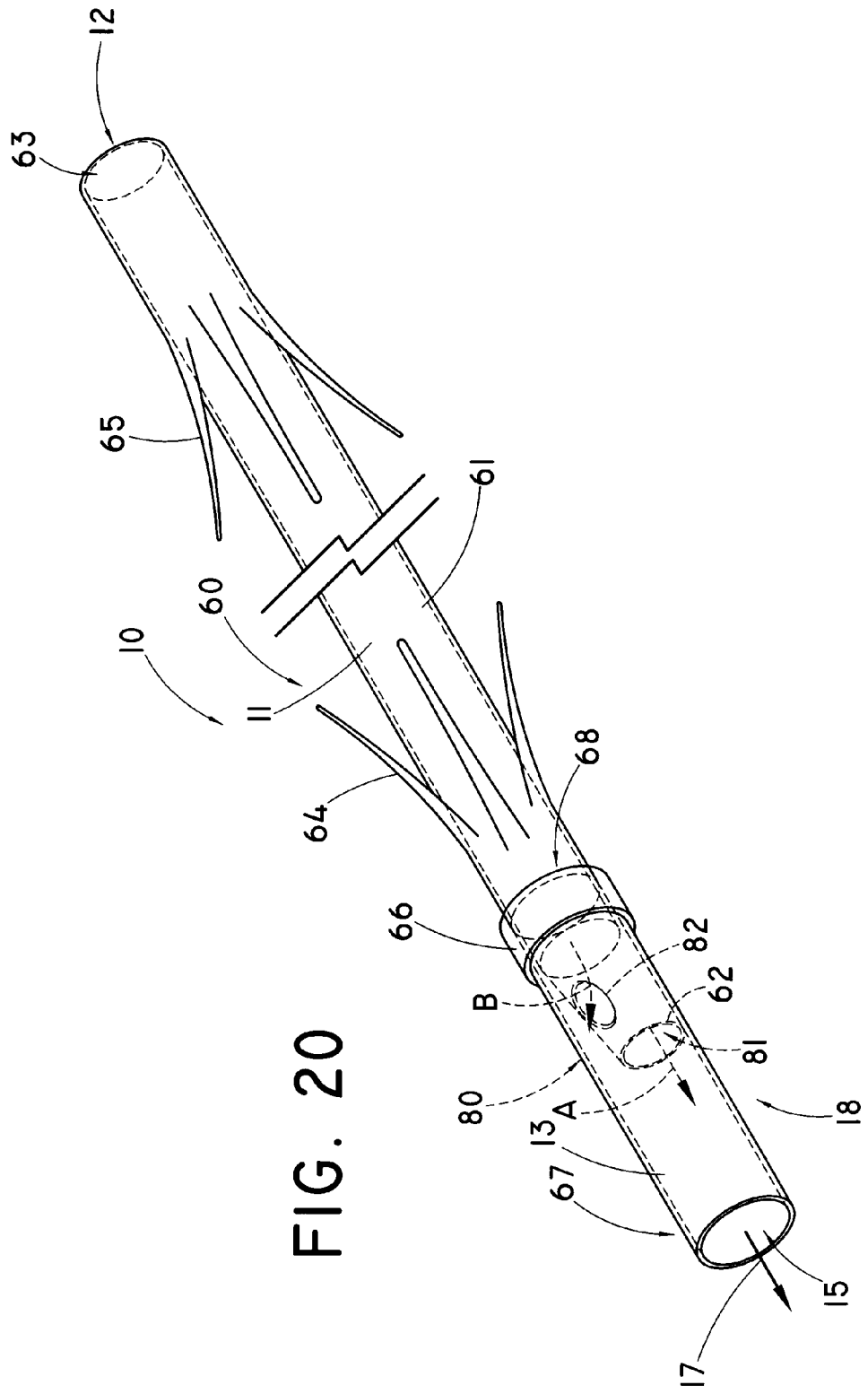
FIG. 20 depicts a pictorial view of an embodiment of the tubular drainage prosthesis shown in FIG. 11 and having a side opening.
Figure 21:
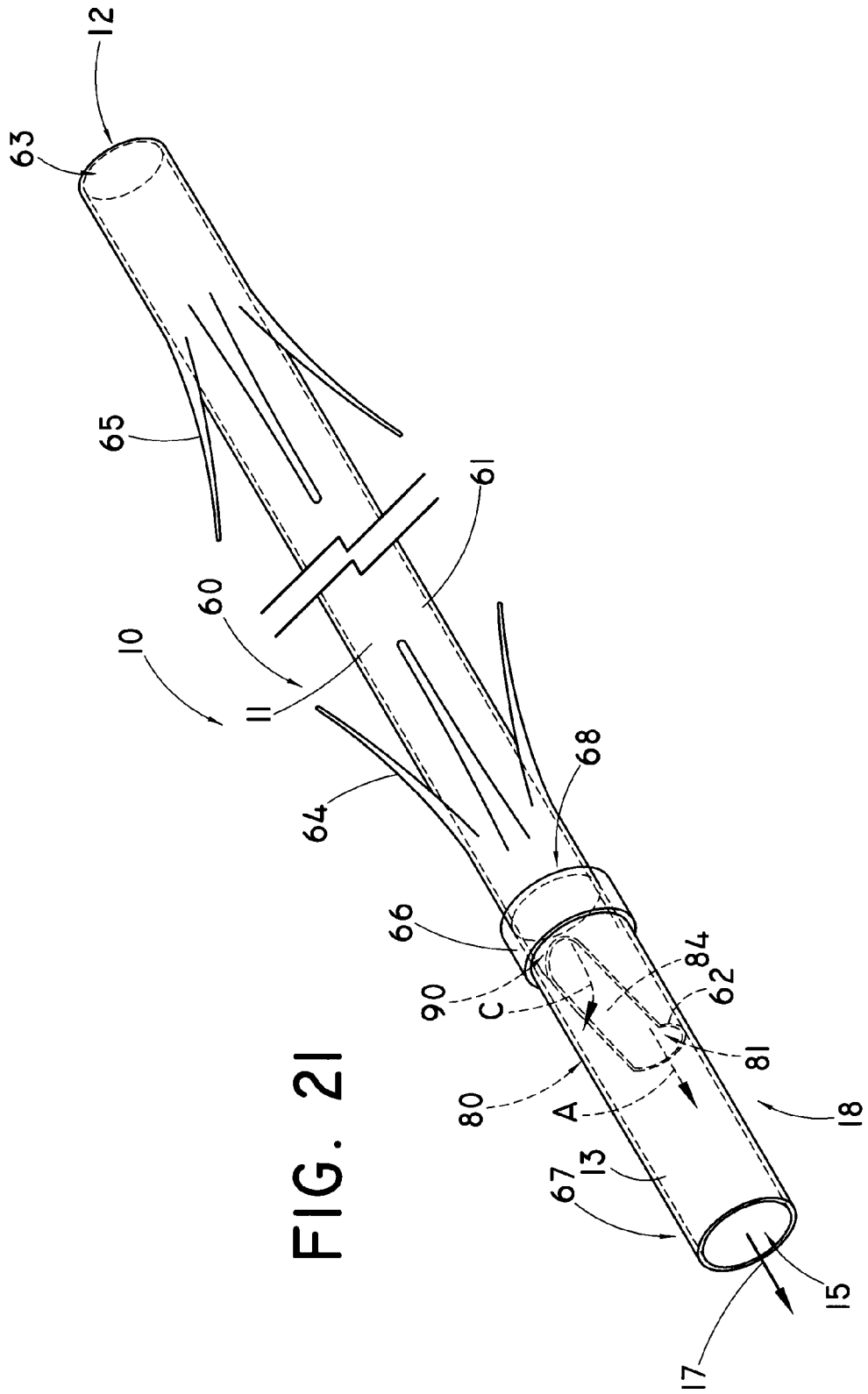
FIG. 21 depicts a pictorial view of an embodiment of the tubular drainage prosthesis of FIG. 11 and having an angled portion at an end of the prosthesis.

In some embodiments, a prosthesis 10 may include a tubular drainage stent 60 having a first end 62 and a collapsible sleeve 13 for drainage into a duct, vessel, organ, etc. and a second end 63 that receives the fluid or other material that is moving under a first, antegrade pressure in the direction 17, similar to the embodiment described above and shown in FIG. 11. As shown in FIGS. 20 and 21, the first end 62 of the tubular drainage stent 60 may include a distal end portion 80 near the first end 62 having one or more openings 82, 84 therethough for allowing fluid to flow through an additional portion of the first end 62. The openings 82, 84 may be configured to allow fluid or other material to flow into the collapsible sleeve 13 when the flow is in the direction 17 in addition to the fluid flow through an opening 81 in the first end 62. The openings 82, 84 also allow flow to continue into the sleeve 13 when the opening 81 in the first end 62 is otherwise occluded and flow is prevented through the opening 81, for example when the first end 62 is abutting the wall of the passageway into which the prosthesis 10 has been implanted. As shown in FIG. 20, the opening 81 includes a flow axis a extending through the opening 81. The opening 82 includes a second flow axis b extending through the opening 82. As shown, the flow axes a and b are non-parallel, demonstrating that the openings 81 and 82 are configured to open in different planes on the stent 60 so that when one opening 81 or 82 is occluded, the other opening 81 or 82 remains open for fluid flow therethrough in the first direction 17. Similarly, as shown in FIG. 21, the opening 84 includes a flow axis c that extends through the opening 84 and is non-parallel with the flow axis a through the opening 81 demonstrating that the openings 81 and 84 are configured to open in different planes on the stent 60 to allow fluid flow to continue in the first direction 17 if any of the openings 81, 84 become occluded.

As discussed above with respect to FIGS. 11-14, the sleeve 13 acts as a one-way valve to prevent retrograde flow through the sleeve 13 and the stent 60. The openings 82, 84 are positioned with respect to the sleeve 13 such that retrograde flow is prevented through the openings 81, 82, 84 and into the stent 60. As shown in FIGS. 20 and 21, the openings 81, 82, 84 are distal to the attachment means 66 of the sleeve 13 on the stent 60 so that the sleeve 13 prevents retrograde flow through the openings 81, 82, 84 and back through the second end 63 of the stent 60.

The openings 82, 84 may be any size and shape that will allow flow to continue from the stent 60 when the first end 62 is occluded. As shown in FIG. 20, the opening 82 may be formed in a side wall 90 of the stent 60 near the first end 62 so that two separate openings 81, 82 are formed in the stent 60. The opening 82 may be round, oval, rectangular, and the like. In some embodiments, a plurality of openings 82 may be included in the stent 60 near the first end 62 (not shown). As shown in FIG. 20, the sleeve 13 may be larger in diameter than the diameter of the first end 62 of the stent 60 so that flow can occur through the opening 82. In some embodiments, the opening 84 may be contiguous with the opening 81, extending from the first end 62 to a side 90 of the stent 60. Similar to the opening 82, the opening 84 allows flow to continue into the sleeve 13 when the opening 81 is occluded. As shown in FIG. 21, the angled opening 84 extends across a portion of the first end 62 and not entirely across the first end 62. The first end 62 is blunted so that the first end 62 of the stent 60 does not pierce the wall as the stent 60 and the wall move against each other. Other shapes and sizes are possible for the openings for example, a rectangular opening may be formed beginning at the first end 62 and extending to the side 90. Any number of openings 84 may be included.

As shown in FIGS. 20 and 21, the prosthesis 10 may include retention means 64, 65 at the first end 62, the second end 63 or both. Alternatively, the prosthesis 10 may include one or more pigtail configurations to retain the stent in position, similar to the pigtail described in FIG. 15. The prosthesis 10 may also include one or more modifications to the sleeve 13 for preventing inversion of the sleeve through the stent in response to the second pressure. For example, the sleeve 13 can be provided with rings, a bell-shaped portion, portions of varying thickness or stiffness, and the like, as described in detail above.

The embodiments described and shown in FIGS. 20 and 21 may be made from the same materials, provided in the same sizes, and delivered to the passageway using the methods described above with reference to FIGS. 11-14. As will be understood by one skilled in the art, any size, shape and materials may be used for the stent and sleeve of the present invention that are suitable for implantation into a body passageway.

As with each of the embodiments of FIGS. 11-16 and 20-21, it is important that the sleeve be made highly flexible and readily collapsible such that normally exists it a closed state, either by a fluid (air or bodily fluids) applying second pressure in a second direction 18 to at least substantially close the sleeve lumen 15 to greatly reduce retrograde migration of fluids, materials, or pathogens, or merely by the absence of fluid applying a first pressure in a first direction 17. In the preferred embodiments the sleeve 13 does not maintain its regular tubular configuration (unless perhaps, it is hanging straight down) due to the inability of the thin polymeric material to support such a configuration against gravitational forces. Rather, it collapses into a closed configuration or self-closes to form a one-way valve due to the material adhering to itself, particularly if wet, or by the atmospheric pressure or fluid pressure in the second direction 18, which typically facilitates its closure.

It is to be understood that the above described anti-reflux esophageal, biliary, an urological prostheses 10 are merely illustrative embodiments of this invention. The present invention can also include other devices, and methods for manufacturing and using them may be devised by those skilled in the art without departing from the spirit and scope of the invention. It is also to be understood that the invention is directed to embodiments both comprising and consisting of disclosed parts. For example, in the esophageal embodiments, it is contemplated that only a portion of the tubular frame need be coated with the sleeve material. Furthermore, the sleeve material extending from the tubular frame can be formed with a different material from that covering the tubular frame. It is also contemplated that the material of the self-expanding stents can be formed of other materials such as nickel titanium alloys commercially known as nitinol, spring steel, and any other spring-like material formed to assume the flexible self-expanding zig-zag stent configuration.

The invention claimed is:

1. A prosthesis for placement in a patient for controlling fluid flow through a passageway, the prosthesis comprising:
a tubular stent having a proximal portion, a distal portion, a passage extending longitudinally therethrough, the distal portion comprising a first opening through a sidewall thereof and a second distal end opening, the first opening defining a first flow axis, the passage comprising a closed tubular conduit between a proximal end and the first opening, the passage defining a second flow axis therethrough non-parallel to the first flow axis, the first flow axis and the second flow axis intersecting at an acute angle; and a sleeve extending from the distal portion of the tubular stent, the sleeve having a lumen extending longitudinally therethrough and communicating with the passage of the tubular stent, the sleeve permitting the passage of a fluid from the passage of the tubular stent through the lumen in a first direction in response to the fluid applying a first pressure to the sleeve in the first direction, the sleeve being collapsible so as to substantially close the lumen in response to a fluid applying a second pressure to the sleeve to prevent flow through the passage of the tubular stent in a retrograde direction;

wherein at least a portion of a proximal portion of the sleeve extends distally over an outer surface of the stent and is affixed to the outer surface of the stent at a sleeve connection position in a fluidly secure configuration so that retrograde flow is prevented through the first and second openings and wherein the first opening is distal to the sleeve connection position, the first opening allows flow to continue into the sleeve when the second opening is occluded; and wherein the sleeve is normally closed in the absence of fluid applying the first pressure to the sleeve in the first direction.

2. The prosthesis of claim 1, wherein the first opening and the second opening are spaced apart.

3. The prosthesis of claim 1, wherein the first opening and the second opening are contiguous.

4. The prosthesis of claim 1, wherein the first opening is configured for permitting fluid flow in the first direction to flow laterally from the passage into the lumen.

5. The prosthesis of claim 1, wherein the stent is non-expanding.

6. The prosthesis of claim 1, wherein the stent comprises at least one retention member for retaining the prosthesis in a body passageway.

7. The prosthesis of claim 6, wherein the at least one retention member comprises a radially extending flap.

8. The prosthesis of claim 6, wherein the at least one retention member comprises a pigtail loop.

9. The prosthesis of claim 1, wherein the sleeve is formed from a polymeric material.

10. The prosthesis of claim 1, wherein the sleeve comprises expanded polytetrafluoroethylene.

11. The prosthesis of claim 1, wherein the sleeve has a thickness between about 0.001 inch to about 0.01 inch.

12. The prosthesis of claim 1, wherein the sleeve comprises a modification for increasing resistance to being inverted through the stent in response to the second pressure.

13. A prosthesis for placement in a patient comprising:

a tubular stent having a passage extending longitudinally therethrough, a side wall opening and a distal end opening connected to the passage, the passage comprising a closed tubular conduit between a proximal end of the stent and the side wall opening; and a sleeve extending from a distal end portion of the tubular stent and having a lumen extending longitudinally therethrough and communicating with the passage of the tubular stent, the sleeve permitting the passage of a fluid through the lumen in a first direction in response to the fluid applying a first pressure to the sleeve in the first direction, the sleeve being collapsible so as to substantially close the lumen in response to a fluid applying a second pressure to the sleeve to prevent flow through the passage of the tubular stent in a retrograde direction;

wherein the side wall opening and the distal end opening are distal to a sleeve connection position on the tubular stent so the sleeve extends over the distal end portion having the side wall opening and the distal end opening and a proximal portion of the sleeve is connected to the stent in a fluidly secure configuration so that retrograde flow is prevented through the side wall opening and the distal end opening; and wherein the side wall opening comprises a first flow axis extending through the side wall opening and the distal end opening comprises a second flow axis extending through the second opening and the second flow axis is non-parallel to the first flow axis, the first flow axis intersects the second flow axis at an acute angle, and wherein the side wall opening allows flow to continue into the sleeve when the distal end opening is occluded.

14. The prosthesis of claim 13, wherein at least a portion of a proximal portion of the sleeve extends over an outer surface of the stent and is affixed thereto at a sleeve connection position.

15. The prosthesis of claim 14, wherein the side wall opening and the distal end opening are positioned distal to the sleeve connection position.

* * * * *